United States Patent
Alibhai et al.

(10) Patent No.: US 8,436,159 B2
(45) Date of Patent: *May 7, 2013

(54) GLYPHOSATE RESISTANT CLASS I 5-ENDOLPYRUVYLSHIKIMATE-3-PHOSPHATE SYNTHASE (EPSPS)

(75) Inventors: Murtaza F. Alibhai, Chesterfield, MO (US); Claire Cajacob, Chesterfield, MO (US); Paul C. C. Feng, Wildwood, MO (US); Gregory R. Heck, Crystal Lake Park, MO (US); Youlin Qi, Chesterfield, MO (US); Stanislaw Flasinski, Chesterfield, MO (US); William C. Stallings, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 284 days.

This patent is subject to a terminal disclaimer.

(21) Appl. No.: 12/688,711

(22) Filed: Jan. 15, 2010

(65) Prior Publication Data

US 2010/0197499 A1   Aug. 5, 2010

Related U.S. Application Data

(62) Division of application No. 10/545,266, filed as application No. PCT/US2004/004636 on Feb. 17, 2004, now Pat. No. 7,723,575.

(60) Provisional application No. 60/448,438, filed on Feb. 18, 2003.

(51) Int. Cl.
*C12N 15/29* (2006.01)
*C12N 15/31* (2006.01)
*C12N 15/32* (2006.01)

(52) U.S. Cl.
USPC .................. 536/23.2; 536/23.6; 536/23.7

(58) Field of Classification Search .................. None
See application file for complete search history.

(56) References Cited

U.S. PATENT DOCUMENTS

| | | | |
|---|---|---|---|
| 4,769,061 A | 9/1988 | Comai | 71/86 |
| 5,633,435 A | 5/1997 | Barry et al. | 800/250 |
| 5,866,775 A * | 2/1999 | Eichholtz et al. | 800/260 |
| 6,040,497 A | 3/2000 | Spencer et al. | 800/288 |
| 6,338,961 B1 * | 1/2002 | DeRose et al. | 435/320.1 |
| 6,566,587 B1 | 5/2003 | Lebrun et al. | 800/300 |
| 6,870,075 B1 | 3/2005 | Beetham et al. | |
| 7,723,575 B2 * | 5/2010 | Alibhai et al. | 800/300 |

FOREIGN PATENT DOCUMENTS

| | | |
|---|---|---|
| AR | 012335 A1 | 10/2000 |
| AR | 025996 A1 | 12/2002 |
| EP | 1 217 073 | 6/2002 |
| WO | WO 97/04103 | 2/1997 |
| WO | WO 98/44140 | 10/1998 |
| WO | WO 98/54330 * | 12/1998 |
| WO | WO 00/66747 | 11/2000 |
| WO | WO 01/66704 | 9/2001 |

OTHER PUBLICATIONS

Town and Kaul 2000, Genbank Accession No. AC084414, Nov. 4, 2000, NCBI, NIH, Bethesda Maryland, USA.*
GenBank Accession No. AC084414, dated Nov. 4, 2000.
Kavanagh et al., "Targeting a foreign protein to chloroplasts using fusions to the transit peptide of a chlorophyll a/b protein," *Mol. and Gen. Genet.*, 215(1):38-45, 1988.
Klee et al., "Cloning of an *Arabidopsis thaliana* gene encoding 5-enolpyruvylshikimate-3-phosphate synthase: sequence analysis and manipulation to obtain glyphosate-tolerant plants," *Mol. And Gen. Genet.*, 210:437-442, 1987.
Office Action date mailed May 13, 2010 in Argentine Patent Application No. P040100492.

* cited by examiner

*Primary Examiner* — David H Kruse
(74) *Attorney, Agent, or Firm* — Dentons US LLP; Pamela Sisson

(57) ABSTRACT

The compositions and methods disclosed herein provide novel DNA molecules that encode glyphosate resistant EPSPS proteins and plants containing these new proteins. The plants that express the new EPSPS proteins are themselves tolerant to the herbicidal effects of glyphosate.

8 Claims, 16 Drawing Sheets

```
    GCGGGTGCCGAAGAAATCGTGCTGCAGCCGATCAAGGAGATCTCCGGCACCGTCAAGCTG
  1 ---------+---------+---------+---------+---------+---------+
    CGCCCACGGCTTCTTTAGCACGACGTCGGCTAGTTCCTCTAGAGGCCGTGGCAGTTCGAC

A  G  A  E  E  I  V  L  Q  P  I  K  E  I  S  G  T  V  K  L

CCGGGGTCCAAGTCGCTTTCCAACCGGATCCTCCTACTCGCCGCCCTGTCCGAGGGGACA
 61 ---------+---------+---------+---------+---------+---------+
    GGCCCCAGGTTCAGCGAAAGGTTGGCCTAGGAGGATGAGCGGCGGGACAGGCTCCCCTGT

P  G  S  K  S  L  S  N  R  I  L  L  A  A  L  S  E  G  T

ACAGTGGTTGATAACCTGCTGAACAGTGAGGATGTCCACTACATGCTCGGGGCCTTGAGG
121 ---------+---------+---------+---------+---------+---------+
    TGTCACCAACTATTGGACGACTTGTCACTCCTACAGGTGATGTACGAGCCCCGGAACTCC

T  V  V  D  N  L  L  N  S  E  D  V  H  Y  M  L  G  A  L  R

ACTCTTGGTCTCTCTGTCGAAGCGGACAAAGCTGCCAAAAGAGCTGTAGTTGTTGGCTGT
181 ---------+---------+---------+---------+---------+---------+
    TGAGAACCAGAGAGACAGCTTCGCCTGTTTCGACGGTTTTCTCGACATCAACAACCGACA

T  L  G  L  S  V  E  A  D  K  A  A  K  R  A  V  V  V  G  C

GGTGGAAAGTTCCCAGTTGAGGATGCTAAAGAGGAAGTGCAGCTCTTCTTGGGGAATGCT
241 ---------+---------+---------+---------+---------+---------+
    CCACCTTTCAAGGGTCAACTCCTACGATTTCTCCTTCACGTCGAGAAGAACCCCTTACGA

G  G  K  F  P  V  E  D  A  K  E  E  V  Q  L  F  L  G  N  A

GGAACTGCAATGCGGCCATTGACAGCAGCTGTTACTGCTGCTGGTGGAAATGCAACTTAC
301 ---------+---------+---------+---------+---------+---------+
    CCTTGACGTTACGCCGGTAACTGTCGTCGACAATGACGACGACCACCTTTACGTTGAATG

G  T  A  M  R  P  L  T  A  A  V  T  A  A  G  G  N  A  T  Y

GTGCTTGATGGAGTACCAAGAATGAGGGAGAGACCCATTGGCGACTTGGTTGTCGGATTG
361 ---------+---------+---------+---------+---------+---------+
    CACGAACTACCTCATGGTTCTTACTCCCTCTCTGGGTAACCGCTGAACCAACAGCCTAAC

V  L  D  G  V  P  R  M  R  E  R  P  I  G  D  L  V  V  G  L

AAGCAGCTTGGTGCAGATGTTGATTGTTTCCTTGGCACTGACTGCCCACCTGTTCGTGTC
421 ---------+---------+---------+---------+---------+---------+
    TTCGTCGAACCACGTCTACAACTAACAAAGGAACCGTGACTGACGGGTGGACAAGCACAG

K  Q  L  G  A  D  V  D  C  F  L  G  T  D  C  P  P  V  R  V

AATGGAATCGGAGGGCTACCTGGTGGCAAGGTCAAGCTGTCTGGCTCCATCAGCAGTCAG
481 ---------+---------+---------+---------+---------+---------+
    TTACCTTAGCCTCCCGATGGACCACCGTTCCAGTTCGACAGACCGAGGTAGTCGTCAGTC

N  G  I  G  G  L  P  G  G  K  V  K  L  S  G  S  I  S  S  Q

TACTTGAGTGCCTTGCTGATGGCTGCTCCTTTGGCTCTTGGGGATGTGGAGATTGAAATC
541 ---------+---------+---------+---------+---------+---------+
    ATGAACTCACGGAACGACTACCGACGAGGAAACCGAGAACCCCTACACCTCTAACTTTAG
```

ATTGATAAATTAATCTCCATTCCGTACGTCGAAATGACATTGAGATTGATGGAGCGTTTT
  601  ---------+---------+---------+---------+---------+---------+
       TAACTATTTAATTAGAGGTAAGGCATGCAGCTTTACTGTAACTCTAACTACCTCGCAAAA

I   D   K   L   I   S   I   P   Y   V   E   M   T   L   R   L   M   E   R   F

GGTGTGAAAGCAGAGCATTCTGATAGCTGGGACAGATTCTACATTAAGGGAGGTCAAAAA
  661  ---------+---------+---------+---------+---------+---------+
       CCACACTTTCGTCTCGTAAGACTATCGACCCTGTCTAAGATGTAATTCCCTCCAGTTTTT

G   V   K   A   E   H   S   D   S   W   D   R   F   Y   I   K   G   G   Q   K

TACAAGTCCCCTAAAAATGCCTATGTTGAAGGTGATGCCTCAAGCGCAAGCTATTTCTTG
  721  ---------+---------+---------+---------+---------+---------+
       ATGTTCAGGGGATTTTTACGGATACAACTTCCACTACGGAGTTCGCGTTCGATAAAGAAC

Y   K   S   P   K   N   A   Y   V   E   G   D   A   S   S   A   S   Y   F   L

GCTGGTGCTGCAATTACTGGAGGGACTGTGACTGTGGAAGGTTGTGGCACCACCAGTTTG
  781  ---------+---------+---------+---------+---------+---------+
       CGACCACGACGTTAATGACCTCCCTGACACTGACACCTTCCAACACCGTGGTGGTCAAAC

A   G   A   A   I   T   G   G   T   V   T   V   E   G   C   G   T   T   S   L

CAGGGTGATGTGAAGTTTGCTGAGGTACTGGAGATGATGGGAGCGAAGGTTACATGGACC
  841  ---------+---------+---------+---------+---------+---------+
       GTCCCACTACACTTCAAACGACTCCATGACCTCTACTACCCTCGCTTCCAATGTACCTGG

Q   G   D   V   K   F   A   E   V   L   E   M   M   G   A   K   V   T   W   T

GAGACTAGCGTAACTGTTACTGGCCCACCGCGGGAGCCATTTGGGAGGAAACACCTCAAG
  901  ---------+---------+---------+---------+---------+---------+
       CTCTGATCGCATTGACAATGACCGGGTGGCGCCCTCGGTAAACCCTCCTTTGTGGAGTTC

E   T   S   V   T   V   T   G   P   P   R   E   P   F   G   R   K   H   L   K

GCGATTGATGTCAACATGAACAAGATGCCTGATGTCGCCATGACTCTTGCTGTGGTTGCC
  961  ---------+---------+---------+---------+---------+---------+
       CGCTAACTACAGTTGTACTTGTTCTACGGACTACAGCGGTACTGAGAACGACACCAACGG

A   I   D   V   N   M   N   K   M   P   D   V   A   M   T   L   A   V   V   A

CTCTTTGCCGATGGCCCGACAGCCATCAGAGACGTGGCTTCCTGGAGAGTAAAGGAGACC
 1021  ---------+---------+---------+---------+---------+---------+
       GAGAAACGGCTACCGGGCTGTCGGTAGTCTCTGCACCGAAGGACCTCTCATTTCCTCTGG

L   F   A   D   G   P   T   A   I   R   D   V   A   S   W   R   V   K   E   T

GAGAGGATGGTTGCGATCCGGACGGAGCTAACCAAGCTGGGAGCATCTGTTGAGGAAGGG
 1081  ---------+---------+---------+---------+---------+---------+
       CTCTCCTACCAACGCTAGGCCTGCCTCGATTGGTTCGACCCTCGTAGACAACTCCTTCCC

```
        CCGGACTACTGCATCATCACGCCGCCGGAGAAGCTGAACGTGACGGCGATCGACACGTAC
1141    ---------+---------+---------+---------+---------+---------+
        GGCCTGATGACGTAGTAGTGCGGCGGCCTCTTCGACTTGCACTGCCGCTAGCTGTGCATG

P   D   Y   C   I   I   T   P   P   E   K   L   N   V   T   A   I   D   T   Y

GACGACCACAGGATGGCGATGGCCTTCTCCCTTGCCGCCTGTGCCGAGGTCCCCGTCACC
1201    ---------+---------+---------+---------+---------+---------+
        CTGCTGGTGTCCTACCGCTACCGGAAGAGGGAACGGCGGACACGGCTCCAGGGGCAGTGG

D   D   H   R   M   A   M   A   F   S   L   A   A   C   A   E   V   P   V   T

ATCCGGGACCCTGGGTGCACCCGGAAGACCTTCCCCGACTACTTCGATGTGCTGAGCACT
1261    ---------+---------+---------+---------+---------+---------+
        TAGGCCCTGGGACCCACGTGGGCCTTCTGGAAGGGGCTGATGAAGCTACACGACTCGTGA

I   R   D   P   G   C   T   R   K   T   F   P   D   Y   F   D   V   L   S   T

TTCGTCAAGAATTAA
1321    ---------+----- 1335
        AAGCAGTTCTTAATT

```
              1                                                      50
petunia   ATAQKPS... EIVLQPIKEI SGTVKLPGSK SLSNRILLLA ALSEGTTVVD
soybean   AAAEKPSTAP EIVLEPIKDI SGTITLPGSK SLSNRILLLA ALSEGTTVVD
  maize   ~~~~~~AGAE EIVLQPIKEI SGTVKLPGSK SLSNRILLLA ALSEGTTVVD
E.coli    ~~~~~~~~ME SLTLQPIARV DGTINLPGSK SVSNRALLLA ALAHGKTVLT 51                                                     100
petunia   NLLSSDDIHY MLGALKTLGL HVEEDSANQR AVVEGCGGLF PVGKESKEEI
soybean   NLLYSEDIHY MLGALRTLGL RVEDDKTTKQ AIVEGCGGLF PTIKESKDEI
  maize   NLLNSEDVHY MLGALRTLGL SVEADKAAKR AVVVGCGGKF PV.EDAKEEV
E.coli    NLLDSDDVRH MLNALTALGV SYTLSADRTR CEIIGNGG.. PLHAEG..AL 101                                                    150
petunia   QLFLGNAGTA MRPLTAAVTV AGGNSRYVLD GVPRMRERPI SDLVDGLKQL
soybean   NLFLGNAGTA MRPLTAAVVA AGGNASYVLD GVPRMRERPI GDLVAGLKQL
  maize   QLFLGNAGTA MRPLTAAVTA AGGNATYVLD GVPRMRERPI GDLVVGLKQL
E.coli    ELFLGNAGTA MRPLAAALCL ..GSNDIVLT GEPRMKERPI GHLVDALRLG 151                                                    200
petunia   GAEVDCFLGT KCPPVRIVSK GGLPGGKVKL SGSISSQYLT ALLMAAPLAL
soybean   GADVDCFLGT NCPPVRVNGK GGLPGGKVKL SGSVSSQYLT ALLMAAPLAL
  maize   GADVDCFLGT DCPPVRVNGI GGLPGGKVKL SGSISSQYLS ALLMAAPLAL
E.coli    GAKITYLEQE NYPPLRL..Q GGFTGGNVDV DGSVSSQFLT ALLMTAPLAP 201                                                    250
petunia   GDVEIEIIDK LISVPYVEMT LKLMERFG.. ISVEHSSSWD RFFVRGGQKY
soybean   GDVEIEIVDK LISVPYVEMT LKLMERFG.. VSVEHSGNWD RFLVHGGQKY
  maize   GDVEIEIIDK LISIPYVEMT LRLMERFG.. VKAEHSDSWD RFYIKGGQKY
E.coli    EDTVIRIKGD LVSKPYIDIT LNLMKTFG.. VEIENQ.HYQ QFVVKGGQSY 251                                                    300
petunia   KSPGKAFVEG DASSASY.FL AGAAVTGGTI TVEGCGTNSL QGDVKFAEVL
soybean   KSPGNAFVEG DASSASY.LL AGAAITGGTI TVNGCGTSSL QGDVKFAEVL
  maize   KSPKNAYVEG DASSASY.FL AGAAITGGTV TVEGCGTTSL QGDVKFAEVL
E.coli    QSPGTYLVEG DASSASY.FL AAAAIKGGTV KVTGIGRNSM QGDIRFADVL
    cp4   LTGQVIDVPG DPSSTAFPLV AALLVPGSDV TILNVLMNPT RTGLIL..TL 301                                                    350
petunia   EKMGAEVTWT ENSVTVKGPP RSSSGRKH.L RAIDVNMNKM P...DVAMTL
soybean   EKMGAKVTWS ENSVTVSGPP RDFSGRKV.L RGIDVNMNKM P...DVAMTL
  maize   EMMGAKVTWT ETSVTVTGPP REPFGRKH.L KAIDVNMNKM P...DVAMTL
E.coli    EKMGATICWG DDYISCT... .....RGE.L NAIDMDMNHI P...DAAMTI
    cp4   QEMGADIEVI NPRLAGGEDV ADLRVRSSTL KGVTVPEDRA PSMIDEYPIL 351                                                    400
petunia   AVVALYADGP TAIRDVASWR VKETERMIAI CTELRKLGAT VEEGPDYCII
soybean   AVVALFANGP TAIRDVASWR VKETERMIAI CTELRKLGAT VEEGPDYCVI
  maize   AVVALFADGP TAIRDVASWR VKETERMVAI RTELTKLGAS VEEGPDYCII
E.coli    ATAALFAKGT TTLRNIYNWR VKETDRLFAM ATELRKVGAE VEEGHDYIRI 401                                                    450
petunia   ..TPPEK... .LNVTDIDTY DDHRMAMAFS LAAC.ADVPV TINDPGCTRK
soybean   ..TPPEK... .LNVTAIDTY DDHRMAMAFS LAAC.GDVPV TIKDPGCTRK
  maize   ..TPPEK... .LNVTAIDTY DDHRMAMAFS LAAC.AEVPV TIRDPGCTRK
E.coli    ..TPPEK... .LNFAEIATY NDHRMAMCFS LVAL.SDTPV TILDPKCTAK
```

FIGURE 2a

```
           451                  474
petunia    TFPNYFDVLQ QYSKH~~~~~ ~~~~
soybean    TFPDYFEVLE RLTKH~~~~~ ~~~~
  maize    TFPDYFDVLS TFVKN~~~~~ ~~~~
 E.coli    TFPDYFEQLA RISQAA~~~~ ~~~~
```

FIGURE 2b

| TIPS | TIPSMut-1-U: 5' C TTC TTG GGG AAT GCT GGA <u>ATT</u> GCA ATG CGG <u>TCA</u> TTG ACA GCA GCT GTT AC 3' (SEQ ID NO:4) |
|---|---|
| | TIPSMut-2-L: 5' GT AAC AGC TGC TGT CAA TGA CCG CAT TGC AAT TCC AGC ATT CCC CAA GAA G 3'(SEQ ID NO:5) |
| T102I | I1-U: 5' GG AAT GCT GGA <u>ATT</u> GCA ATG CG 3'(SEQ ID NO:6) |
| | I2-L: 5' CG CAT TGC <u>AAT</u> TCC AGC ATT CC 3'(SEQ ID NO:7) |
| P106T | mEmut-9-U: 5' GCT GGA ACT GCA ATG CGG <u>ACA</u> TTG ACA GCA GCT GTT AC 3'(SEQ ID NO:8) |
| | mEmut-10-L: 5' GT AAC AGC TGC TGT CAA <u>TGT</u> CCG CAT TGC AGT TCC AGC 3'(SEQ ID NO:9) |
| P106S | mEmut-7-U: GCTGGAACTGCAATGCGGtCATTGACAGCAGCTGTTAC (SEQ ID NO:10) |
| | mEmut-8-L: GTAACAGCTGCTGTCAATGaCCGCATTGCAGTTCCAGc (SEQ ID NO:11) |
| P106L | H1-U: CAATGCGGCTATTGACAGCAGC (SEQ ID NO:12) |
| | H2-L: GCTGCTGTCAATAGCCGCATTG (SEQ ID NO:13) |
| P106G | P106G-U: GCAATGCGGggATTGACAGCAG (SEQ ID NO:14) |
| | P106G-L: CTGCTGTCAATccCCGCATTGC (SEQ ID NO:15) |
| P106A | P106A-U: GCAATGCGGgCATTGACAGCAG (SEQ ID NO:16) |
| | P106A-L: CTGCTGTCAATGcCCGCATTGC (SEQ ID NO:17) |
| P106V | P106V-U: GCAATGCGGgtATTGACAGCAG (SEQ ID NO:18) |
| | P106V-L: CTGCTGTCAATacCCGCATTGC (SEQ ID NO:19) |
| P106L | P106L-U: GCAATGCGGctgTTGACAGCAGCTG (SEQ ID NO:20) |
| | P106L-L: CAGCTGCTGTCAAcagCCGCATTGC (SEQ ID NO:21) |
| P106I | P106I-U: GCAATGCGGAtcTTGACAGCAGC (SEQ ID NO:22) |
| | P106I-L: GCTGCTGTCAAgaTCCGCATTGC (SEQ ID NO:23) |
| P106M | P106M-U: GCAATGCGGAtgTTGACAGCAGC (SEQ ID NO:24) |
| | P106M-L: GCTGCTGTCAAcaTCCGCATTGC (SEQ ID NO:25) |

FIGURE 4a

| P106C | P106C-U: GCAATGCGGtgtTTGACAGCAGCTG (SEQ ID NO:26) |
|---|---|
| | P106C-L: CAGCTGCTGTCAAacaCCGCATTGC (SEQ ID NO:27) |

| ZmAroA-1 | AATAGCATGCCCGGCGCCGAGGAGATCGTGCTGCAGCCCATCAAGGAGATC (SEQ ID NO:40) |
|---|---|
| ZmAroA-2 | ATTGAATTCGAGCTCATTAATTCTTGACGAAAGTGCTC (SEQ ID NO:41) |
| ZmAroA-3 | GTTTCCACGGCGTGCATGgCCGGCGCCGAGGAGATCG (SEQ ID NO:42) |
| ZmAroA-4 | CGATCTCCTCGGCGCCGGcCATGCACGCCGTGGAAAC (SEQ ID NO:43) |

FIGURE 4b

GLYPHOSATE RESISTANT CLASS I 5-ENDOLPYRUVYLSHIKIMATE-3-PHOSPHATE SYNTHASE (EPSPS)

This application is a divisional of U.S. application Ser. No. 10/545,266, filed Aug. 10, 2005, now U.S. Pat. No. 7,723,575, the disclosure of which is incorporated herein by reference in its entirety; which is a 371 application of PCT/US2004/004636, filed Feb. 17, 2004, which application claims benefit of U.S. Provisional Application No. 60/448,438, filed Feb. 18, 2003, the entire contents of which are incorporated by reference herein.

FIELD OF THE INVENTION

This invention relates to plant molecular biology and plant genetic engineering for herbicide resistance and, more particularly, to class I 5-enolpyruvylshikimate-3-phosphate synthases modified for glyphosate resistance. Plant genetic engineering methods are used to modify class I 5-enolpyruvylshikimate-3-phosphate synthase DNA and the encoded proteins, and to transfer these molecules into plants of agronomic importance. More specifically, the invention comprises DNA and protein compositions of glyphosate resistant 5-enolpyruvylshikimate-3-phosphate synthases, and to the plants containing these compositions.

BACKGROUND OF THE INVENTION

N-phosphonomethylglycine, also known as glyphosate, is a well-known herbicide that has activity on a broad spectrum of plant species. Glyphosate is the active ingredient of Roundup® (Monsanto Co., St Louis, Mo.), a herbicide having a long history of safe use and a desirably short half-life in the environment. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the class I 5-enolpyruvyishikimate-3-phosphate synthase (EPSPS) found in plants and some bacteria. Glyphosate tolerance in plants can be achieved by the expression of a modified class I EPSPS that has lower affinity for glyphosate, yet still retains its catalytic activity in the presence of glyphosate (U.S. Pat. Nos. 4,535,060, and 6,040,497). "Tolerant" or "tolerance" refers to a reduced effect of an agent on the growth and development, and yield of a plant, in particular, tolerance to the phytotoxic effects of a herbicide, especially glyphosate.

Enzymes, such as, class II EPSPSs have been isolated from bacteria that are naturally resistant to glyphosate and when the enzyme is expressed as a transgene in plants provides glyphosate tolerance to the plants (U.S. Pat. Nos. 5,633,435 and 5,094,945). Enzymes that degrade glyphosate in plant tissues (U.S. Pat. No. 5,463,175) are also capable of conferring plant tolerance to glyphosate. DNA constructs that contain the necessary genetic elements to express the glyphosate resistant enzymes or degradative enzymes create chimeric transgenes useful in plants. Such transgenes are used for the production of transgenic crops that are tolerant to glyphosate, thereby allowing glyphosate to be used for effective weed control with minimal concern of crop damage. For example, glyphosate tolerance has been genetically engineered into corn (U.S. Pat. No. 5,554,798), wheat (Zhou et al. Plant Cell Rep. 15:159-163, 1995), soybean (WO 9200377) and canola (WO 9204449). The transgenes for glyphosate tolerance and transgenes for tolerance to other herbicides, for example the bar gene (Sh.Bar) may be included in DNA constructs for use as a selectable marker for plant transformation (present invention pMON81519; and Toki et al. Plant Physiol., 100: 1503-1507, 1992; Thompson et al. EMBO J. 6:2519-2523, 1987; phosphinothricin acetyltransferase DeBlock et al. EMBO J., 6:2513-2522, 1987, glufosinate herbicide) are also useful as selectable markers or scorable markers and can provide a useful phenotype for selection of transgenic plants when the marker gene is linked with other agronomically useful traits.

Development of herbicide-tolerant crops has been a major breakthrough in agriculture biotechnology as it has provided farmers with new weed control methods. One enzyme that has been successfully engineered for resistance to its inhibitor herbicide is class I EPSPS. Variants of class I EPSPS have been isolated (Pro-Ser, U.S. Pat. No. 4,769,061; Gly-Ala, U.S. Pat. No. 4,971,908; Gly-Ala, Gly-Asp, U.S. Pat. No. 5,310,667; Gly-Ala, Ala-Thr, U.S. Pat. No. 5,8866,775) that are resistant to glyphosate. However, many EPSPS variants either do not demonstrate a sufficiently high $K_i$ for glyphosate or have a $K_m$ for phosphoenol pyruvate (PEP) too high to be effective as a glyphosate resistance enzyme for use in plants (Padgette et. al, In "Herbicide-resistant Crops", Chapter 4 pp 53-83. ed. Stephen Duke, Lewis Pub, CRC Press Boca Raton, Fla. 1996). However, one class I EPSPS variant, T102I/P106S (TIPS) that is operably linked to a heterologous promoter has been shown to provide glyphosate tolerance to transgenic maize plants (U.S. Pat. No. 6,040,497). A glyphosate tolerant EPSPS has also been isolated from the weed *Eleusine indica* [WO 01/66704].

There is a need in the field of plant molecular biology for a diversity of genes that can provide a positive selectable marker phenotype. In particular, glyphosate tolerance is used extensively as a positive selectable marker in plants and is a valuable phenotype for use in crop production. The stacking and combining of existing transgene traits with newly developed traits is enhanced when distinct positive selectable marker genes are used. The marker genes provide either a distinct phenotype, such as, antibiotic or herbicide tolerance, or a molecular distinction discernable by methods used for DNA detection. The transgenic plants can be screened for the stacked traits by analysis for multiple antibiotic or herbicide tolerance or for the presence of novel DNA molecules by DNA detection methods. The present invention provides DNA and protein compositions of glyphosate resistant variant class I EPSP synthases. The present invention also provides DNA constructs useful in plants and transgenic plants that exhibit glyphosate tolerance.

SUMMARY OF THE INVENTION

In one aspect of the invention there is provided an isolated modified EPSPS DNA molecule encoding a glyphosate tolerant EPSPS protein having an isoleucine or leucine at position 102, and an amino acid at position 106 selected from the group consisting of threonine, glycine, cysteine, alanine, and isoleucine. In another aspect of the invention is a DNA construct that comprises a promoter that functions in plant cells operably linked to a modified EPSPS DNA molecule encoding a glyphosate tolerant EPSPS protein having an isoleucine or leucine at position 102, and an amino acid at position 106 selected from the group consisting of threonine, glycine, cysteine, alanine, and isoleucine. In yet another aspect of the invention there is provided a transgenic plant than contains the DNA construct, wherein the transgenic plant is tolerant to glyphosate herbicide.

In another aspect of the invention is a method of preparing a fertile transgenic plant comprising providing a plant expression cassette having a modified EPSPS gene encoding an EPSPS protein having isoleucine or leucine at position 102, and an amino acid at position 106 selected from the group consisting of threonine, glycine, cysteine, alanine, and isoleucine; and contacting recipient plant cells with the plant expression cassette under conditions permitting the uptake of the plant expression cassette by the recipient cells; and selecting the recipient plant cells that contain the plant expression cassette; and regenerating plants from the selected recipient plant cells; and identifying a fertile transgenic plant that is tolerant to glyphosate.

In another aspect of the invention is a fertile glyphosate tolerant transgenic plant that contains a plant expression cassette having a modified plant EPSPS gene encoding an EPSPS protein having isoleucine or leucine at position 102, and an amino acid at position 106 selected from the group consisting of threonine, glycine, cysteine, alanine, and isoleucine that is crossed to another plant to provide progeny that are tolerant to glyphosate.

In another aspect of the invention, there is provided a method for controlling weeds in a field of crop plants, wherein the field of crop plants is treated with an effective amount of a glyphosate containing herbicide and the crop plants contain a plant expression cassette having a modified EPSPS gene encoding an EPSPS protein having isoleucine or leucine at position 102, and an amino acid at position 106 selected from the group consisting of threonine, glycine, cysteine, alanine, and isoleucine.

BRIEF DESCRIPTION OF THE DRAWINGS

FIG. 1. Polynucleotide and polypeptide sequence of maize EPSPS.

FIG. 2. Polypeptide alignment of class I plant and bacterial EPSP synthases.

FIG. 4. DNA primer sequences

DETAILED DESCRIPTION OF THE INVENTION

Figure 3:
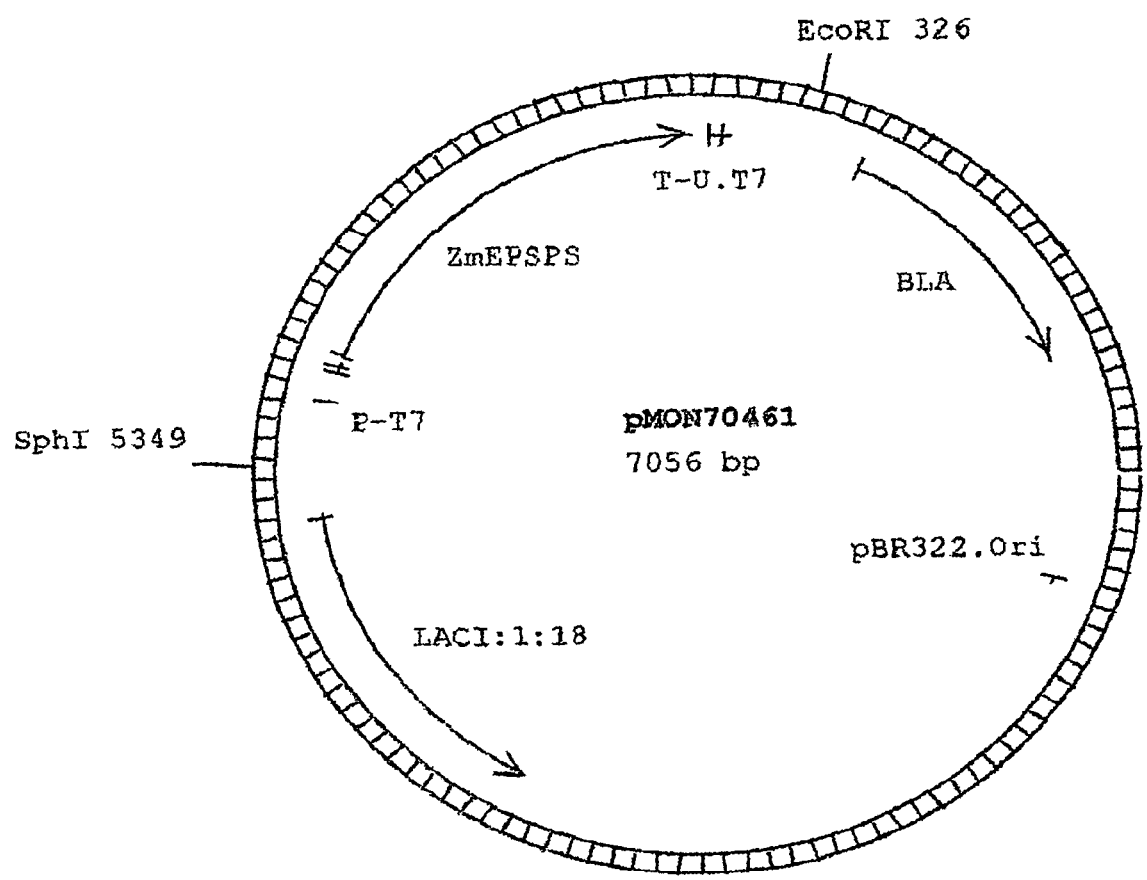
FIG. 3. DNA construct map of pMON70461 (wild-type EPSPS).

The present invention is based, in part, on the construction of a glyphosate resistant EPSPS and utilizing DNA molecules that encode the EPSPS in a DNA construct to provide herbicide tolerance to transgenic plants expressing the glyphosate resistant EPSPS in its tissues. The following descriptions are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, (1991); and Lewin, Genes V, Oxford University Press: New York, (1994). The nomenclature for DNA bases as set forth at 37 CFR §1.822 is used. "Nucleic acid" refers to deoxyribonucleic acid (DNA) and ribonucleic acid (RNA). The standard one- and three-letter nomenclature for amino acid residues is used.

Methods of the present invention include designing EPSPS proteins that confer a glyphosate tolerant trait to the plant into which they are introduced. Polynucleotide molecules encoding proteins involved in herbicide tolerance are known in the art, and include, but are not limited to a polynucleotide molecule encoding 5-enolpyruvylshikimate-3-phosphate synthase (EPSPS, described in U.S. Pat. Nos. 5,627,061, 5,633, 435, and 6,040,497; Padgette et al. Herbicide Resistant Crops, Lewis Publishers, 53-85, 1996; and Penaloza-Vazquez, et al. Plant Cell Reports 14:482-487, 1995; and aroA (U.S. Pat. No. 5,094,945) for glyphosate tolerance.

"Glyphosate" refers to N-phosphonomethylglycine and its' salts. Glyphosate is the active ingredient of Roundup® herbicide (Monsanto Co.). Plant treatments with "glyphosate" refer to treatments with the Roundup® or Roundup Ultra® herbicide formulation, unless otherwise stated. Glyphosate as N-phosphonomethylglycine and its' salts (not formulated Roundup® herbicide) are components of synthetic culture media used for the selection of bacteria and plant tolerance to glyphosate or used to determine enzyme resistance in in vitro biochemical assays. Examples of commercial formulations of glyphosate include, without restriction, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt.

Through plant genetic engineering methods, it is possible to produce glyphosate tolerant plants by inserting into the plant genome a DNA molecule that causes the production of higher levels of wild-type EPSPS (U.S. Pat. No. 4,940,835; Shah et al., Science 233:478-481, 1986). Glyphosate tolerance can also be achieved by the expression of EPSPS variants that have lower affinity for glyphosate and therefore retain their catalytic activity in the presence of glyphosate, for example, aroA P-S (U.S. Pat. No. 5,094,945), CP4 EPSPS (U.S. Pat. No. 5,633,435), maize TIPS (U.S. Pat. No. 6,040, 497), 101/192 and 101/144 variants (U.S. Pat. No. 5,866,775 and U.S. Pat. No. 6,225,112, Howe et al., Mol. Breeding. 10:153-164, 2002). For example, glyphosate tolerance has been genetically engineered into corn (U.S. Pat. Nos. 5,554, 798, 6,040,497), wheat (Zhou et al. Plant Cell Rep. 15:159-163, 1995), soybean (WO 9200377), cotton (WO 0234946), and canola (WO 9204449).

Variants of the wild-type EPSPS enzyme have been isolated that are glyphosate-resistant as a result of alterations in the EPSPS amino acid coding sequence (Kishore et al., Annu. Rev. Biochem. 57:627-663, 1988; Schulz et al., Arch. Microbiol. 137:121-123, 1984; Sost et al., FEBS Lett. 173:238-241, 1984; Kishore et al., In "Biotechnology for Crop Protection" ACS Symposium Series No. 379. eds. Hedlin et al., 37-48, 1988). These variants typically have a higher $K_i$ for glyphosate than the wild-type EPSPS enzyme that confers the glyphosate-tolerant phenotype, but these variants are also characterized by a high $K_m$ for PEP that makes the enzyme kinetically less efficient. For example, the apparent $K_m$ for PEP and the apparent $K_i$ for glyphosate for the native EPSPS from *E. coli* are 10 µM and 0.5 µM while for a glyphosate-resistant isolate having a single amino acid substitution of an alanine for the glycine at position 96 these values are 220 µM and 4.0 mM, respectively. U.S. Pat. No. 6,040,497 reports that the EPSPS variant, known as the TIPS mutation (a substitution of isoleucine for threonine at amino acid position 102 and a substitution of serine for proline at amino acid position 106) comprises two mutations that when introduced into the polypeptide sequence of *Zea mays* EPSPS confers glyphosate resistance to the enzyme. Transgenic plants containing this mutant enzyme are tolerant to glyphosate. Identical mutations may be made in the genes encoding glyphosate sensitive EPSPS enzymes from other sources to create glyphosate resistant enzymes. In vitro site-directed mutagenesis of DNA molecules have clearly demonstrated utility for introducing specific changes in a DNA sequence of a genome and other methods under development may also provide in situ site-directed mutagenesis methods (US Patent Pub. 20020151072). These methods may be used to generate the DNA coding sequences that encode for the glyphosate resistant EPSPS variants of the present invention in the context of the endogenous host cell EPSPS gene.

The present invention provides amino acid substitutions in a class I EPSPS that demonstrates enhanced glyphosate resistance over any previously described modified class I EPSPSs. The present invention relates specifically to certain double variants of class I EPSPSs that are glyphosate resistant, but still retain a functional level of PEP substrate binding activity. During the development of the novel double variants of class I EPSPSs for glyphosate resistance, it was necessary to construct a number of single variants useful as controls for the assay and for demonstration that the double variant is necessary to obtain both a glyphosate resistant enzyme and an enzyme that still retains a sufficient level of substrate binding activity to serve as a functional replacement for a native class I EPSPS.

The EPSPS enzyme functions in plant chloroplast, therefore, chloroplast transit peptides (CTP) are engineered in a DNA molecule to encode a fusion of the CTP to the N terminus of an EPSPS creating a chimeric molecule. A chimeric polynucleic acid coding sequence is comprised of two or more open reading frames joined in-frame that encode a chimeric protein, for example, a chloroplast transit peptide and an EPSPS enzyme. A chimeric gene refers to the multiple genetic elements derived from heterologous sources operably linked to comprise a gene. The CTP directs the glyphosate resistant enzyme into the plant chloroplast. In the native plant EPSPS gene, chloroplast transit peptide regions are contained in the native coding sequence (for example, CTP2, Klee et al., Mol. Gen. Genet. 210:47-442, 1987). The CTP is cleaved from the EPSPS enzyme at the chloroplast membrane to create a "mature EPSPS or EPSPS enzyme" that refers to the polypeptide sequence of the processed protein product remaining after the chloroplast transit peptide has been removed.

The native CTP may be substituted with a heterologous CTP during construction of a transgene plant expression cassette. Many chloroplast-localized proteins, including EPSPS, are expressed from nuclear genes as precursors and are targeted to the chloroplast by a chloroplast transit peptide (CTP) that is removed during the import steps. Examples of other such chloroplast proteins include the small subunit (SSU) of ribulose-1,5-bisphosphate carboxylase (rubisco), ferredoxin, ferredoxin oxidoreductase, the light-harvesting complex protein I and protein H, and thioredoxin F. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as, the *Arabidopsis thaliana* EPSPS CTP (Klee et al., Mol. Gen. Genet. 210:437-442 (1987), and the *Petunia hybrida* EPSPS CTP (della-Cioppa et al., Proc. Natl. Acad. Sci. USA 83:6873-6877 (1986) has been shown to target heterologous EPSPS protein to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. No. 5,627,061, U.S. Pat. No. 5,633,435, U.S. Pat. No. 5,312,910, EP 0218571, EP 189707, EP 508909, and EP 924299). Those skilled in the art will recognize that various chimeric constructs can be made that utilize the functionality of a particular CTP to import glyphosate resistant EPSPS enzymes into the plant cell chloroplast.

Modification and changes may be made in the structure of the DNA polynucleotides of the invention and still obtain a DNA molecule that transcribes a mRNA that encodes the modified functional EPSPS protein of the present invention. The amino acid substitutions disclosed herein provide an improved characteristic to the protein, for example, enhanced glyphosate resistant EPSP synthase. Amino-acid substitutions or amino-acid variants, are preferably substitutions of a single amino-acid residue for another amino-acid residue at one or more positions within the protein. Substitutions, deletions, insertions or any combination thereof can be combined to arrive at a final construct. The present invention involves the substitution of amino acids in a class I EPSPS protein to provide a new feature of the protein, such as, glyphosate resistance.

It is known that the genetic code is degenerate. The amino acids and their RNA codon(s) are listed below in Table 1.

TABLE 1

Amino acids and the RNA codons that encode them.

| Amino Acid Full name; 3 letter code; 1 letter code | Codons |
| --- | --- |
| Alanine; Ala; A | GCA GCC GCG GCU |
| Cysteine; Cys; C | UGC UGU |
| Aspartic acid; Asp; D | GAC GAU |
| Glutamic acid; Glu; E | GAA GAG |
| Phenylalanine; Phe; F | UUC UUU |
| Glycine; Gly; G | GGA GGC GGG GGU |
| Histidine; His; H | CAC CAU |
| Isoleucine; Ile; I | AUA AUC AUU |
| Lysine; Lys; K | AAA AAG |
| Leucine; Leu; L | UUA UUG CUA CUC CUG CUU |
| Methionine; Met; M | AUG |
| Asparagine; Asn; N | AAC AAU |
| Proline; Pro; P | CCA CCC CCG CCU |
| Glutamine; Gln; Q | CAA CAG |
| Arginine; Arg; R | AGA AGG CGA CGC CGG CGU |
| Serine; Ser; S | AGC AGU UCA UCC UCG UCU |
| Threonine; Thr; T | ACA ACC ACG ACU |
| Valine; Val; V | GUA GUC GUG GUU |
| Tryptophan; Trp; W | UGG |
| Tyrosine; Tyr; Y | UAC UAU |

The codons are described in terms of RNA bases, for example adenine, uracil, guanine and cytosine, it is the mRNA that is directly translated into polypeptides. It is understood that when designing a DNA polynucleotide for use in a construct, the DNA bases would be substituted, for example, thymine instead of uracil. Codon refers to a sequence of three nucleotides that specify a particular amino acid. Codon usage or "codon bias" refers to the frequency of use of codons encoding amino acids in the coding sequences of organisms. A codon usage table would be consulted when selecting substituting codons for an artificial DNA sequence. The sequence of codons provides a coding sequence that refers to the region of continuous sequential nucleic acid triplets encoding a protein, polypeptide, or peptide sequence. The term "encoding DNA" refers to chromosomal DNA, plasmid DNA, cDNA, or artificial DNA polynucleotide that encodes any of the proteins discussed herein. "Plasmid" refers to a circular, extrachromosomal, self-replicating piece of DNA.

The term "endogenous" refers to materials originating from within an organism or cell. "Exogenous" refers to materials originating from outside of an organism or cell. This typically applies to nucleic acid molecules used in producing transformed or transgenic host cells and plants.

The term "genome" as it applies to bacteria encompasses both the chromosome and plasmids within a bacterial host cell. Encoding nucleic acids of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. The term "gene" refers to polynucleic acids that comprise chromosomal DNA, plasmid DNA, cDNA, an artificial DNA polynucleotide, or other DNA that is transcribed into an RNA molecule, wherein the RNA may encode a peptide, polypeptide, or protein, and the genetic elements flanking the coding sequence that are involved in the regulation of expression of the mRNA or polypeptide of the present invention. A "fragment" of a gene is a portion of a full-length polynucleic acid molecule that is of at least a minimum length capable of transcription into a RNA, translation into a peptide, or useful as a probe or primer in a DNA detection method.

Polynucleic acids of the present invention introduced into plant cells can therefore be either chromosomally-integrated or organelle-localized. The modified EPSPSs of the present invention are targeted to the chloroplast by a chloroplast transit peptide located at the N-terminus of the coding sequence. Alternatively, the gene encoding the modified EPSPSs may be integrated into the chloroplast genome, thereby eliminating the need for a chloroplast transit peptide.

"Heterologous DNA" sequence refers to a polynucleotide sequence that originates from a foreign source or species or, if from the same source, is modified from its original form. "Homologous DNA" refers to DNA from the same source as that of the recipient cell.

"Hybridization" refers to the ability of a strand of nucleic acid to join with a complementary strand via base pairing. Hybridization occurs when complementary sequences in the two nucleic acid strands bind to one another. The nucleic acid probes and primers of the present invention hybridize under stringent conditions to a target DNA sequence. Any conventional nucleic acid hybridization or amplification method can be used to identify the presence of DNA from a transgenic event in a sample. A transgenic "event" is produced by transformation of a plant cell with heterologous DNA, i.e., a nucleic acid construct that includes a transgene of interest; regeneration of a population of plants resulting from the insertion of the transgene into the genome of the plant cell, and selection of a particular plant characterized by insertion into a particular genome location. The term "event" refers to the original transformant plant and progeny of the transformant that include the heterologous DNA. The term "event" also includes progeny produced by a sexual outcross between the event and another plant that wherein the progeny includes the heterologous DNA. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., Molecular Cloning—A Laboratory Manual, 2nd. ed., Cold Spring Harbor Laboratory, Cold Spring Harbor, N.Y. (1989), herein referred to as Sambrook et al., (1989), and by Haymes et al., In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (such as, to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa, (Nucl. Acids Res. 12:203-213, 1984); and Wetmur and Davidson, (J. Mol. Biol. 31:349-370, 1988). Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, for example, one will select relatively low salt and/or high temperature conditions, such as provided by about 0.02 M to about 0.15 M NaCl at temperatures of about 50° C. to about 70° C. A stringent condition, for example, is to wash the hybridization filter at least twice with high-stringency wash buffer (0.2×SSC, 0.1% SDS, 65° C.). Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA molecules via hybridization is well known to those of skill in the art, and the teachings of U.S. Pat. Nos. 4,965,188 and 5,176,995 are exemplary of the methods of hybridization analyses.

"Identity" refers to the degree of similarity between two polynucleic acid or protein sequences. An alignment of the two sequences is performed by a suitable computer program. A widely used and accepted computer program for performing sequence alignments is CLUSTALW v1.6 (Thompson, et al. Nucl. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between 200 and 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

"Intron" refers to a genetic element that is a portion of a gene not translated into protein, even though it is transcribed into RNA, the intron sequence being "spliced out" from the mature messenger RNA.

An "isolated" nucleic acid molecule is substantially separated away from other nucleic acid sequences with which the nucleic acid is normally associated, such as, from the chromosomal or extrachromosomal DNA of a cell in which the nucleic acid naturally occurs. A nucleic acid molecule is an isolated nucleic acid molecule when it comprises a transgene or part of a transgene present in the genome of another organism. The term also embraces nucleic acids that are biochemically purified so as to substantially remove contaminating nucleic acids and other cellular components. The term "transgene" refers to any polynucleic acid molecule normative to a cell or organism transformed into the cell or organism. "Transgene" also encompasses the component parts of a native plant gene modified by insertion of a normative polynucleic acid molecule by directed recombination or site specific mutation.

"Isolated," "Purified," "Homogeneous" polypeptides. A polypeptide is "isolated" if it has been separated from the cellular components (nucleic acids, lipids, carbohydrates, and other polypeptides) that naturally accompany it or that is chemically synthesized or recombinant. A polypeptide molecule is an isolated polypeptide molecule when it is expressed from a transgene in another organism. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods. Proteins can be purified by any of the means known in the art, for example as described in Guide to Protein Purification, ed. Deutscher, Meth. Enzymol. 185, Academic Press, San Diego, 1990; and Scopes, Protein Purification: Principles and Practice, Springer Verlag, New York, 1982.

The term "native" generally refers to a naturally-occurring ("wild-type") polynucleic acid or polypeptide. However, in the context of the present invention a modification of a native isolated polynucleotide and polypeptide has occurred to provide a variant polypeptide with a particular phenotype, for example, amino acid substitution in a native glyphosate sensitive EPSPS to provide a glyphosate resistant EPSPS. The polynucleotide modified in this manner is normative with respect to the genetic elements normally found linked to a naturally occurring unmodified polynucleotide.

Using well-known methods, the skilled artisan can readily produce nucleotide and amino acid sequence variants of genes and proteins that provide a modified gene product. For example, "variant" DNA molecules of the present invention are DNA molecules containing changes in an EPSPS coding sequence, such as, changes that include one or more nucleotides of a native EPSPS coding sequence being deleted, added, and/or substituted, such that the variant EPSPS gene encodes a modified protein that retains EPSPS activity and is now resistant to glyphosate herbicide. Variant DNA molecules can be produced, for example, by standard DNA mutagenesis techniques or by chemically synthesizing the variant DNA molecule or a portion thereof. Methods for chemical synthesis of nucleic acids are discussed, for example, in Beaucage et al., Tetra. Letts. 22:1859-1862 (1981), and Matteucci et al., J. Am. Chem. Soc. 103:3185-(1981). Chemical synthesis of nucleic acids can be performed, for example, on automated oligonucleotide synthesizers. Such variants preferably do not change the reading frame of the protein-coding region of the nucleic acid. The present invention also encompasses fragments of a protein that lacks at least one residue of a full-length protein, but that substantially maintains activity of the protein.

A first nucleic-acid molecule is "operably linked" with a second nucleic-acid molecule when the first nucleic-acid molecule is placed in a functional relationship with the second nucleic-acid molecule. For example, a promoter is operably linked to a protein-coding nucleic acid sequence if the promoter effects the transcription or expression of the coding sequence. Generally, operably linked DNA molecules are contiguous and, where necessary to join two protein-coding regions, in reading frame.

The term "plant" encompasses any higher plant and progeny thereof, including monocots (for example, corn, rice, wheat, barley, etc.), dicots (for example, soybean, cotton, canola, tomato, potato, *Arabidopsis*, tobacco, etc.), gymnosperms (pines, firs, cedars, etc.) and includes parts of plants, including reproductive units of a plant (for example, seeds, bulbs, tubers, fruit, flowers, etc.) or other parts or tissues from that the plant can be reproduced.

"Polyadenylation signal" or "polyA signal" refers to a nucleic acid sequence located 3' to a coding region that causes the addition of adenylate nucleotides to the 3' end of the mRNA transcribed from the coding region.

"Polymerase chain reaction (PCR)" refers to a DNA amplification method that uses an enzymatic technique to create multiple copies of one sequence of nucleic acid (amplicon). Copies of a DNA molecule are prepared by shuttling a DNA polymerase between two amplimers. The basis of this amplification method is multiple cycles of temperature changes to denature, then re-anneal amplimers (DNA primer molecules), followed by extension to synthesize new DNA strands in the region located between the flanking amplimers. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention.

The term "promoter" or "promoter region" refers to a polynucleic acid molecule that functions as a regulatory element, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant DNA construct, as demonstrated by its ability to produce mRNA.

A "recombinant" nucleic acid is made by a combination of two otherwise separated segments of nucleic acid sequence, for example, by chemical synthesis or by the manipulation of isolated segments of polynucleic acids by genetic engineering techniques. The term "recombinant DNA construct" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs may be constructed to be capable of expressing antisense RNAs, or stabilized double stranded antisense RNA in order to inhibit expression of a specific target RNA of interest.

"Resistance" refers to an enzyme that is able to function in the presence of a toxin, for example, naturally occurring glyphosate resistant class II EPSP synthases resistant to glyphosate or a modified EPSPS enzyme having catalytic activity that is unaffected by at a herbicide concentration that normally disrupts the same activity in the wild type enzyme, for example, the modified class I EPSP synthases of the present invention. An enzyme that has resistance to a herbicide may also have the function of detoxifying the herbicide, for example, phosphinothricin acetyltransferase, and glyphosate oxidoreductase.

"Selectable marker" refers to a polynucleic acid molecule that encodes a protein, which confers a phenotype facilitating identification of cells containing the polynucleic acid molecule. Selectable markers include those genes that confer resistance to antibiotics (for example, ampicillin, kanamycin), complement a nutritional deficiency (for example, uracil, histidine, leucine), or impart a visually distinguishing characteristic (for example, color changes or fluorescence). Useful dominant selectable marker genes include genes encoding antibiotic resistance genes (for example, neomycin phosphotransferase, npt); and herbicide resistance genes (for example, phosphinothricin acetyltransferase, class II EPSP synthase, modified class I EPSP synthase). A useful strategy for selection of transformants for herbicide resistance is described, for example, in Vasil, Cell Culture and Somatic Cell Genetics of Plants, Vols. I-III, Laboratory Procedures and Their Applications Academic Press, New York (1984).

An "artificial polynucleotide" as used in the present invention is a DNA sequence designed according to the methods of the present invention and created as an isolated DNA molecule for use in a DNA construct that provides expression of a protein in host cells, or for the purposes of cloning into appropriate constructs or other uses known to those skilled in the art. Computer programs are available for these purposes, including but not limited to the "BestFit" or "Gap" programs of the Sequence Analysis Software Package, Genetics Computer Group (GCG), Inc., University of Wisconsin Biotechnology Center, Madison, Wis. 53711. The artificial polynucleotide may be created by a one or more methods known in the art, that include, but are not limited to: overlapping PCR. An artificial polynucleotide as used herein, is non-naturally occurring and can be substantially divergent from other polynucleotides that code for the identical or nearly identical protein.

Expression of a Modified Class I EPSPS Coding Sequence in Plants

DNA constructs are made that contain various genetic elements necessary for the expression of the EPSPS coding sequence in plants. "DNA construct" refers to the heterologous genetic elements operably linked to each other making up a recombinant DNA molecule and may comprise elements that provide expression of a DNA polynucleotide molecule in a host cell and elements that provide maintenance of the construct in the host cell. A plant expression cassette comprises the operable linkage of genetic elements that when transferred into a plant cell provides expression of a desirable gene product. "Plant expression cassette" refers to chimeric DNA segments comprising the regulatory elements that are operably linked to provide the expression of a transgene product in plants. Promoters, leaders, introns, transit peptide encoding polynucleic acids, 3' transcriptional termination regions are all genetic elements that may be operably linked by those skilled in the art of plant molecular biology to provide a desirable level of expression or functionality to a glyphosate resistant class I EPSPS of the present invention. A DNA construct can contain one or more plant expression cassettes expressing the DNA molecules of the present invention or other DNA molecules useful in the genetic engineering of crop plants.

A variety of promoters specifically active in vegetative tissues, such as leaves, stems, roots and tubers, can be used to express the EPSPS polynucleic acid molecules of the present invention. Examples of tuber-specific promoters include, but are not limited to the class I and II patatin promoters (Bevan et al., EMBO J. 8:1899-1906, 1986; Koster-Topfer et al., Mol Gen Genet. 219:390-396, 1989; Mignery et al., Gene. 62:27-44, 1988; Jefferson et al., Plant Mol. Biol. 14: 995-1006, 1990), the promoter for the potato tuber ADPGPP genes, both the large and small subunits; the sucrose synthase promoter (Salanoubat and Belliard, Gene. 60:47-56, 1987; Salanoubat and Belliard, Gene 84: 181-185, 1989); and the promoter for the major tuber proteins including the 22 kd protein complexes and proteinase inhibitors (Hannapel, Plant Physiol.

101:703-704, 1993). Examples of leaf-specific promoters include, but are not limited to the ribulose biphosphate carboxylase (RBCS or RuBISCO) promoters (see, for example, Matsuoka et al., Plant J. 6:311-319, 1994); the light harvesting chlorophyll a/b binding protein gene promoter (see, for example, Shiina et al., Plant Physiol. 115:477-483, 1997; Casal et al., Plant Physiol. 116:1533-1538, 1998); and the *Arabidopsis thaliana* myb-related gene promoter (Atmyb5) (Li et al., FEBS Lett. 379:117-121, 1996). Examples of root-specific promoter include, but are not limited to the promoter for the acid chitinase gene (Samac et al., Plant Mol. Biol. 25:587-596, 1994); the root specific subdomains of the CaMV35S promoter that have been identified (Lam et al., Proc. Natl. Acad. Sci. (U.S.A.) 86:7890-7894, 1989); the ORF13 promoter from *Agrobacterium rhizogenes* that exhibits high activity in roots (Hansen et al., Mol. Gen. Genet. 254:337-343 (1997); the promoter for the tobacco root-specific gene TobRB7 (Yamamoto et al., Plant Cell 3:371-382, 1991); and the root cell specific promoters reported by Conkling et al. (Conkling et al., Plant Physiol. 93:1203-1211, 1990).

Another class of useful vegetative tissue-specific promoters is meristematic (root tip and shoot apex) promoters. For example, the "SHOOTMERISTEMLESS" and "SCARECROW" promoters, which are active in the developing shoot or root apical meristems can be used (Di Laurenzio et al., Cell 86:423-433, 1996; Long, Nature 379:66-69, 1996). Another example of a useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, for example, Enjuto et al., Plant Cell. 7:517-527, 1995). Also another example of a useful promoter is that which controls the expression of knI-related genes from maize and other species that show meristem-specific expression (see, for example, Granger et al., Plant Mol. Biol. 31:373-378, 1996; Kerstetter et al., Plant Cell 6:1877-1887, 1994; Hake et al., Philos. Trans. R. Soc. Lond. B. Biol. Sci. 350:45-51, 1995). Another example of a meristematic promoter is the *Arabidopsis thaliana* KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, for example, Lincoln et al., Plant Cell 6:1859-1876, 1994).

Suitable seed-specific promoters can be derived from the following genes: MAC1 from maize (Sheridan et al., Genetics 142:1009-1020, 1996; Cat3 from maize (GenBank No. L05934, Abler et al., Plant Mol. Biol. 22:10131-1038, 1993); viviparous-1 from *Arabidopsis* (Genbank No. U93215); Atimyc1 from *Arabidopsis* (Urao et al., Plant Mol. Biol. 32:571-57, 1996; Conceicao et al., Plant 5:493-505, 1994); napA from *Brassica napus* (GenBank No. J02798); the napin gene family from *Brassica napus* (Sjodahl et al., Planta 197:264-271, 1995, and others (Chen et al., Proc. Natl. Acad. Sci. 83:8560-8564, 1986).

The ovule-specific promoter for BEL1 gene can also be used (Reiser et al. Cell 83:735-742, 1995, GenBank No. U39944; Ray et al, Proc. Natl. Acad. Sci. USA 91:5761-5765, 1994). The egg and central cell specific MEA (FIS1) and FIS2 promoters are also useful reproductive tissue-specific promoters (Luo et al., Proc. Natl. Acad. Sci. USA, 97:10637-10642, 2000; Vielle-Calzada, et al., Genes Dev. 13:2971-2982, 1999).

A maize pollen-specific promoter has been identified in maize (Guerrero et al., Mol. Gen. Genet. 224:161-168, 1990). Other genes specifically expressed in pollen have been described (see, for example, Wakeley et al., Plant Mol. Biol. 37:187-192, 1998; Ficker et al., Mol. Gen. Genet. 257:132-142, 1998; Kulikauskas et al., Plant Mol. Biol. 34:809-814, 1997; Treacy et al., Plant Mol. Biol. 34:603-611, 1997).

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436. It is further recognized that the exact boundaries of regulatory sequences may not be completely defined, DNA fragments of different lengths may have identical promoter activity.

The translation leader sequence means a DNA molecule located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences include maize and petunia heat shock protein leaders, plant virus coat protein leaders, plant rubisco gene leaders among others (Turner and Foster, Molecular Biotechnology 3:225, 1995).

The "3' non-translated sequences" means DNA sequences located downstream of a structural polynucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (nos 3'; Fraley et al., Proc. Natl. Acad. Sci. USA 80: 4803-4807, 1983). The use of different 3' non-translated sequences is exemplified by Ingelbrecht et al., Plant Cell 1:671-680, 1989.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al. (1989).

The DNA construct of the present invention may be introduced into the genome of a desired plant host by a variety of conventional transformation techniques that are well known to those skilled in the art. "Transformation" refers to a process of introducing an exogenous polynucleic acid molecule (for example, a DNA construct, a recombinant polynucleic acid molecule) into a cell or protoplast and that exogenous polynucleic acid molecule is incorporated into a host cell genome or an organelle genome (for example, chloroplast or mitochondria) or is capable of autonomous replication. "Transformed" or "transgenic" refers to a cell, tissue, organ, or organism into which a foreign polynucleic acid, such as a DNA vector or recombinant polynucleic acid molecule. A "transgenic" or "transformed" cell or organism also includes progeny of the cell or organism and progeny produced from a breeding program employing such a "transgenic" plant as a parent in a cross and exhibiting an altered phenotype resulting from the presence of the foreign polynucleic acid molecule.

Methods of transformation of plant cells or tissues include, but are not limited to *Agrobacterium* mediated transformation method and the Biolistics or particle-gun mediated transformation method. Suitable plant transformation vectors for the purpose of *Agrobacterium* mediated transformation include those elements derived from a tumor inducing (Ti) plasmid of *Agrobacterium tumefaciens*, for example, right border (RB) regions and left border (LB) regions, and others disclosed by Herrera-Estrella et al., Nature 303:209 (1983); Bevan, Nucleic Acids Res. 12:8711-8721 (1984); Klee et al., Bio-Technology 3(7):637-642 (1985). In addition to plant transformation vectors derived from the Ti or root-inducing (Ri) plasmids of *Agrobacterium*, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

DNA constructs can be prepared that incorporate the class I EPSPS variant coding sequences of the present invention for use in directing the expression of the sequences directly from the host plant cell plastid. Examples of such constructs suitable for this purpose and methods that are known in the art and are generally described, for example, in Svab et al., Proc. Natl. Acad. Sci. USA 87:8526-8530, (1990) and Svab et al., Proc. Natl. Acad. Sci. USA 90:913-917 (1993) and in U.S. Pat. No. 5,693,507. It is contemplated that plastid transformation and expression of the class I EPSPS variants of the present invention will provide glyphosate tolerance to the plant cell.

A plasmid expression vector suitable for the introduction of a polynucleic acid encoding a polypeptide of present invention in monocots using electroporation or particle-gun mediated transformation is composed of the following: a promoter that is constitutive or tissue-specific; an intron that provides a splice site to facilitate expression of the gene, such as the maize Hsp70 intron (U.S. Pat. No. 5,593,874); and a 3' polyadenylation sequence such as the nopaline synthase 3' sequence (T-nos 3'; Fraley et al., Proc. Natl. Acad. Sci. USA 80: 4803-4807, 1983). This expression cassette may be assembled on high copy replicons suitable for the production of large quantities of DNA.

When adequate numbers of cells containing the exogenous polynucleic acid molecule encoding polypeptides from the present invention are obtained, the cells can be cultured, then regenerated into whole plants. "Regeneration" refers to the process of growing a plant from a plant cell (for example, plant protoplast or explant). Such regeneration techniques rely on manipulation of certain phytohormones in a tissue culture growth medium, typically relying on a biocide and/or herbicide marker that has been introduced together with the desired nucleotide sequences. Choice of methodology for the regeneration step is not critical, with suitable protocols being available for hosts from Leguminoseae (for example, alfalfa, soybean, clover), Umbelliferae (carrot, celery, parsnip), Cruciferae (for example, cabbage, radish, canola/rapeseed), Cucurbitaceae (for example, melons and cucumber), Gramineae (for example, wheat, barley, rice, maize), Solanaceae (for example, potato, tobacco, tomato, peppers), various floral crops, such as sunflower, and nut-bearing trees, such as almonds, cashews, walnuts, and pecans. See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Such regeneration techniques are described generally in Klee et al., Ann. Rev. Plant Phys. 38:467-486 (1987).

The development or regeneration of transgenic plants containing the exogenous polynucleic acid molecule that encodes a polypeptide of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants.

Plants that can be made to have enhanced glyphosate tolerance by practice of the present invention include, but are not limited to, *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The following examples are provided to better elucidate the practice of the present invention and should not be interpreted in any way to limit the scope of the present invention. Those skilled in the art will recognize that various modifications, additions, substitutions, truncations, etc., can be made to the methods and genes described herein while not departing from the spirit and scope of the present invention.

EXAMPLES

Example 1

Site-Directed Mutagenesis of a Class I EPSPS

Mutagenesis of a DNA molecule encoding a class I EPSPS was directed at a region of the protein defined by a polypeptide sequence -G-T-$X_1$-$X_2$-R-P- (SEQ ID NO:1) of the class I EPSPS, where $X_1$ and $X_2$ are any amino acid. The invention described herein provides for the mutagenesis of a gene encoding a class I EPSPS, wherein the mutagenesis results in a polypeptide sequence of -G-$X_4$-$X_1$-$X_2$-R-$X_3$- (SEQ ID NO:2) in this region of the class I EPSPS protein related to the binding of the enzyme substrate and the glyphosate molecule. The amino acid substitutions in SEQ ID NO:1 that will result in a glyphosate resistant class I EPSPS include replacing the native threonine (T) at $X_4$ with amino acids isoleucine (I) or leucine (L), and replacing the native proline (P) at $X_3$ with threonine, glycine, cysteine, alanine, or isoleucine. The amino acid positions 102 and 106 are designated according to the maize EPSPS polypeptide sequence shown in FIG. 1, however, other plant class I EPSPS coding sequences (FIG. 2), for example, petunia and soybean can be used as templates for site-directed mutagenesis as the relative positions of the threonine and proline amino acids, respectively, are conserved; however, a slightly different amino acid position number in the EPSPS polypeptide sequence may occur because of variations in the starting point of mature EPSPSs from various sources (U.S. Pat. No. 5,866,775, FIG. 1), those variations are recognized by those skilled in the art and are within the scope of the present invention. In a similar manner, site-directed mutagenesis of prokaryote class I EPSPS DNA coding sequences, for example, *E. coli* (FIG. 2) can be performed using mutagenesis primers designed to hybridize to these DNA molecules to create the EPSPS variants -G-$X_4$-$X_1$-$X_2$-R-$X_3$- (SEQ ID NO:2) as described herein.

Figure 9:
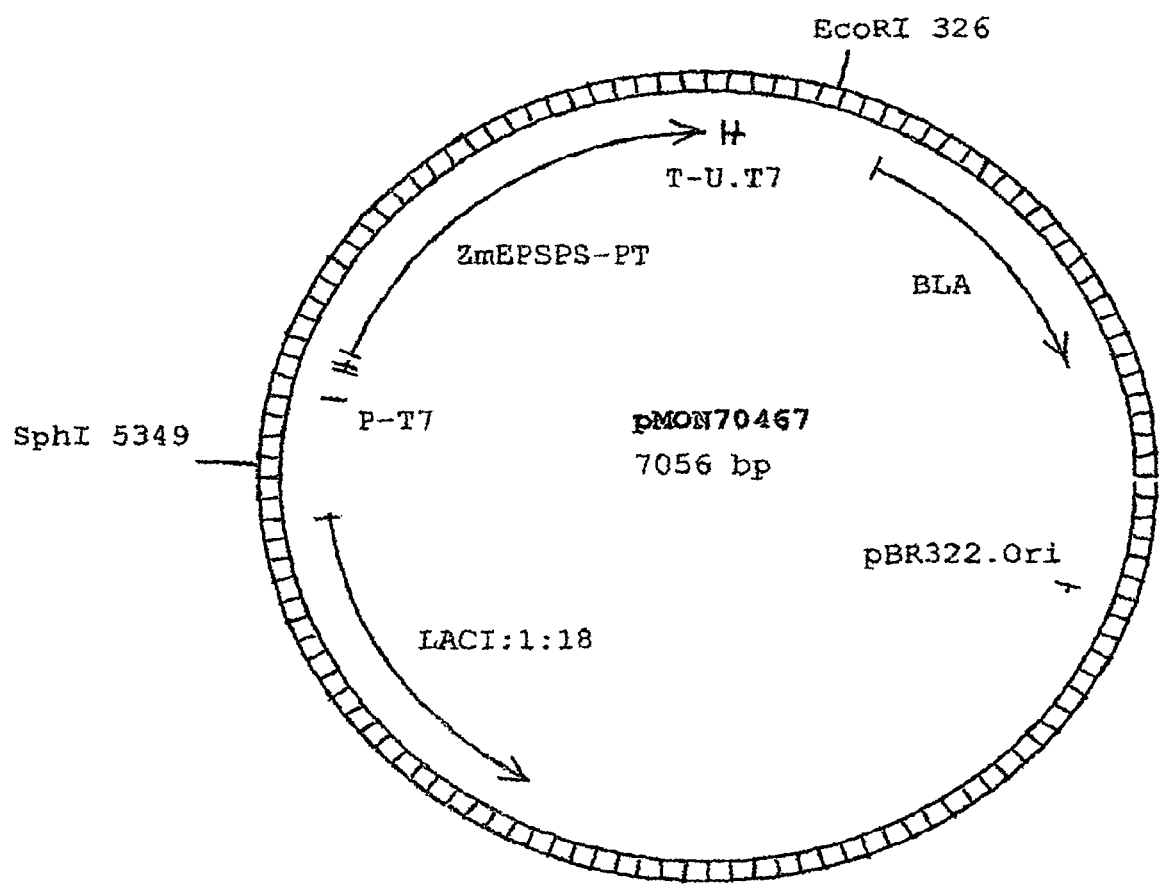
FIG. 9. DNA construct map of pMON70467 (ZmPT variant)

Mutations were made using plant EPSPS DNA coding sequence template as an example of class I EPSPSs. Mutations of the DNA coding sequence result in variant EPSPS protein molecules by the substitution of codons (Table 1) encoding for amino acids in the DNA sequence. The variant protein sequences that have two amino acid substitutions compared to the wild type protein sequence are referred to as double variants, a single amino acid substitution is referred to as a single variant. All the variants were made using the PCR-based QuickChange™ Site-directed Mutagenesis Kit (Stratagene, La Jolla, Calif., Cat. No. 200518) following the manufactures instructions. The DNA sequence of each mutagenesis primer was designed, and then ordered from Invitrogen Corp., Custom Primers (Carlsbad, Calif.). Mutagenesis of a maize wild-type DNA molecule (SEQ ID NO:3) encoding the EPSPS enzyme was performed using pMON70461 (FIG. 3) as the template. pMON70461 contains the unmodified wild-type maize EPSPS coding sequence. The previously known T102I, P106S variant (TIPS) was created by the PCR mediated mutagenesis method using primer pairs, TIPSMut-1-U (SEQ ID NO:4) and TIPSMut-2-L (SEQ ID NO:5) as shown in FIG. 4A, and is contained in pMON70462 plasmid. The single EPSPS variants were created by mutagenesis of the maize wild-type EPSPS DNA coding sequence as controls for measuring the efficacy of the double variant EPSPSs. The following single EPSPS variants were created using PCR mutagenesis: the T102I variant (primers I1-U (SEQ ID NO:6) and I2-L (SEQ ID NO:7), pMON58455), the P106T variant (primers mEmut-9-U (SEQ ID NO:8) and mEmut-10-L (SEQ ID NO:9), pMON70467, FIG. 9), the P106S variant (primers mEmut-7-U (SEQ ID NO:10) and mEmut-8-L (SEQ ID NO:11), pMON70466), and the P106L variant (primers H1-U (SEQ ID NO:12) and H2-L (SEQ ID NO:13), pMON58451) were created using the unmodified wild-type maize EPSPS coding sequence contained in pMON70461 as the template for site directed mutagenesis.

Figure 5:
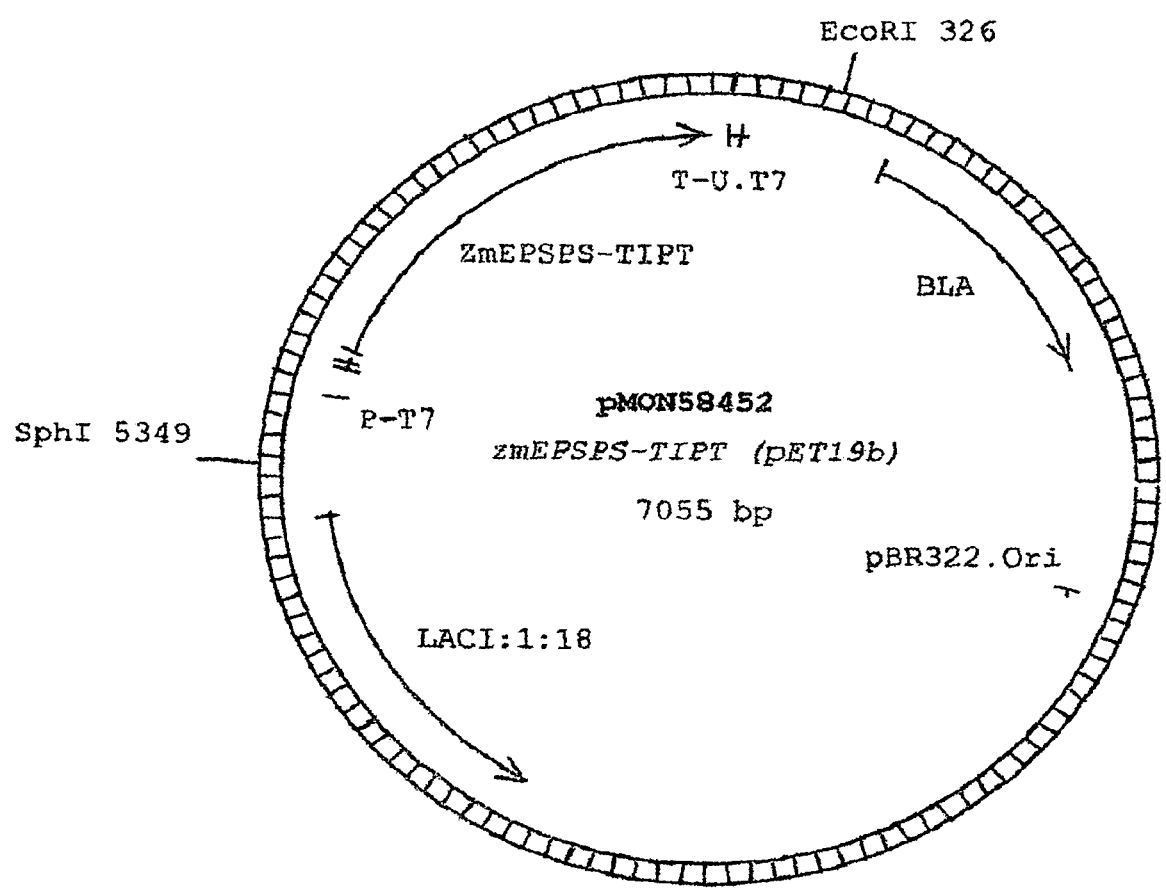
FIG. 5. DNA construct map of pMON58452 (ZmTIPT variant)

The double variants of the present invention were made using pMON58452 (FIG. 5) as the template. This pMON58452 EPSPS gene template contains the maize EPSPS double variant T102I, P106T (TIPT) that was constructed by mutagenesis of pMON70467 with the mutagenesis primers mEmut-9-U and mEmut-10-L. The various mutagenesis primer sequences were designed and then were synthesized by Invitrogen Corp., Custom Primers and used in combination in a PCR to create the variant EPSPS coding sequences. The PCR was set up in a 50 µl reaction in the following manner: $dH_2O$ 38 µl; 2 mM dNTP 1 µL; 10× buffer 5 µL; pMON58452 1 µL (10 ng); primer-U 2 µL; primer-L 2 µL; pfu Turbo enzyme 1 µL. PCR was carried out on a MJ Research PTC-200 thermal cycler using the following program: Step 1—94° C. for 30 seconds; Step 2—94° C. for 30 seconds; Step 3—55° C. for 1 minute; Step 4—68° C. for 14 minute; Step 5—go to step 2, 16 times; Step 6—End. At the end of the PCR, 1 µl of the restriction enzyme DpnI was added to each 50 µl of PCR reaction and the mixture was incubated at 37° C. for 1 hour. The proline (106) amino acid codon of pMON58452 was substituted in subsequent steps to provide additional variants that include TWO (primer P106G-U, SEQ ID NO:14 and -L, SEQ ID NO:15), TIPA (primer P106A-U, SEQ ID NO:16 and -L, SEQ ID NO:17), TIPV (primer P106V-U, SEQ ID NO:18 and -L, SEQ ID NO:19), TIPL (primer P106L-U, SEQ ID NO:20 and -L, SEQ ID NO:21), TIPI (primer P106I-U, SEQ ID NO:22 and -L, SEQ ID NO:23), TIPM (primer P106M-U, SEQ ID NO:24 and -L, SEQ ID NO:25), and TIPC (primer P106C-U, SEQ ID NO:26 and -L, SEQ ID NO:27). The mutagenesis primers' DNA sequences are shown in FIGS. 4A and 4B. The double variants of the gene encoding the EPSPS protein were generated using the PCR conditions described above.

At the end of the PCR, 1 µl of the restriction enzyme DpnI was added to each 50 µl of PCR reaction and the mixture was incubated at 37° C. for 1 hour. DpnI is a methylation- and hemimethylation-specific restriction enzyme and will cleave only those double-stranded DNA plasmid containing at least one wild-type, methylated, strand, leaving the mutated plasmid intact. After the DpnI treatment, 1 µl of the treated reaction mixture was used to transform the competent *E. coli* strain XL1-blue (Stratagene Corp, La Jolla, Calif.) following the manufacturer's instruction. The transformed cells were plated onto a Petri dish containing carbenicillin at a final concentration of 0.1 mg/mL. The dish was then incubated at 37° C. overnight. Single colonies were picked the next day and used to inoculate a 3 mL liquid culture containing 0.1 mg/mL carbenicillin. The liquid culture was incubated overnight at 37° C. with agitation at 250 rpm. Plasmid DNA was prepared from 1 mL of the liquid culture using Qiagen's miniprep Kit (Qiagen Corp. Cat. No. 27160). The DNA was eluted in 50 µl of $dH_2O$. The entire coding region of three independent clones from each mutagenesis was sequenced by DNA sequence analysis (ABI Prism™ 377, PE Biosystems, Foster City, Calif. and DNASTAR sequence analysis software, DNASTAR Inc., Madison, Wis.) and confirmed to contain the desired mutation.

Other plant class I EPSPS coding sequences were modified to contain the TIPA variant. The EPSPS coding sequence of *Arabidopsis thaliana* (Columbia) EPSPS1 and EPSPS coding sequences of lettuce (*Lactuca sativa*) were isolated for mutagensis. RT-PCT was used to isolate the coding sequence of the mature protein of both AtEPSPS1 and lettuce EPSPS. All of the primers were ordered from Invitrogen. The leaf tissues of both *Arabidopsis* and lettuce were ground into powder in liquid nitrogen with a mortar and pestle. Total RNA was isolated using Qiagene's RNeasy mini kit (cat. #74904) using 10 mg leaf powder and RNA was eluted into 50 µl water. RT-PCR reactions were performed using one-step-RT-PCR kit (Invitrogen #10928-034) in a 50 µL reaction containing: $dH_2O$ 24 µL; reaction buffer 50 µL; total RNA 20 µL; AtEPSPS-F primer (SEQ ID NO:28) (10 µM) 1 µL; AtEPSPS-R (SEQ ID NO:29) (10 µM) 1 µL; Taq 1 µL. RT-PCR was carried out on a MJ Research PTC-200 thermal cycler using the following program: Step 1—40° C. for 30 seconds; Step 2—94° C. for 2 minutes; Step 3—94° C. for 20 seconds; Step 4—65° C. for 30 seconds; Step 5—68° C. for 1 minute 30 seconds; Step 6—go to step 3, 30 times; Step 7—End. Both PCR reactions yielded an approximately 1.3 kilo base band on a 1 percent agarose electrophoresis gel. The lettuce EPSPS coding sequence was isolated using the primers LsEPSPS-F (SEQ ID NO:30) and LsEPSPS-R (SEQ ID NO:31) in the above described method. The RT-PCR products were cloned into PCR-II vector (Invitrogen Corp.) and the DNA molecules sequenced.

Figure 11:
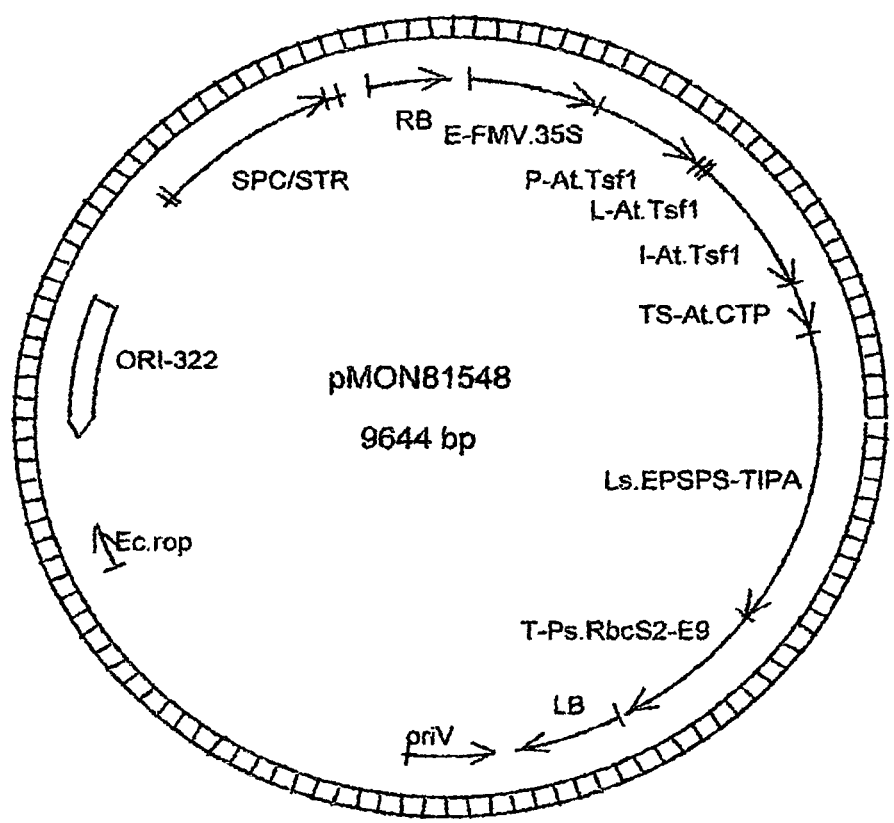
FIG. 11. DNA construct map of pMON81548 (LsTIPA variant)
Figure 12:
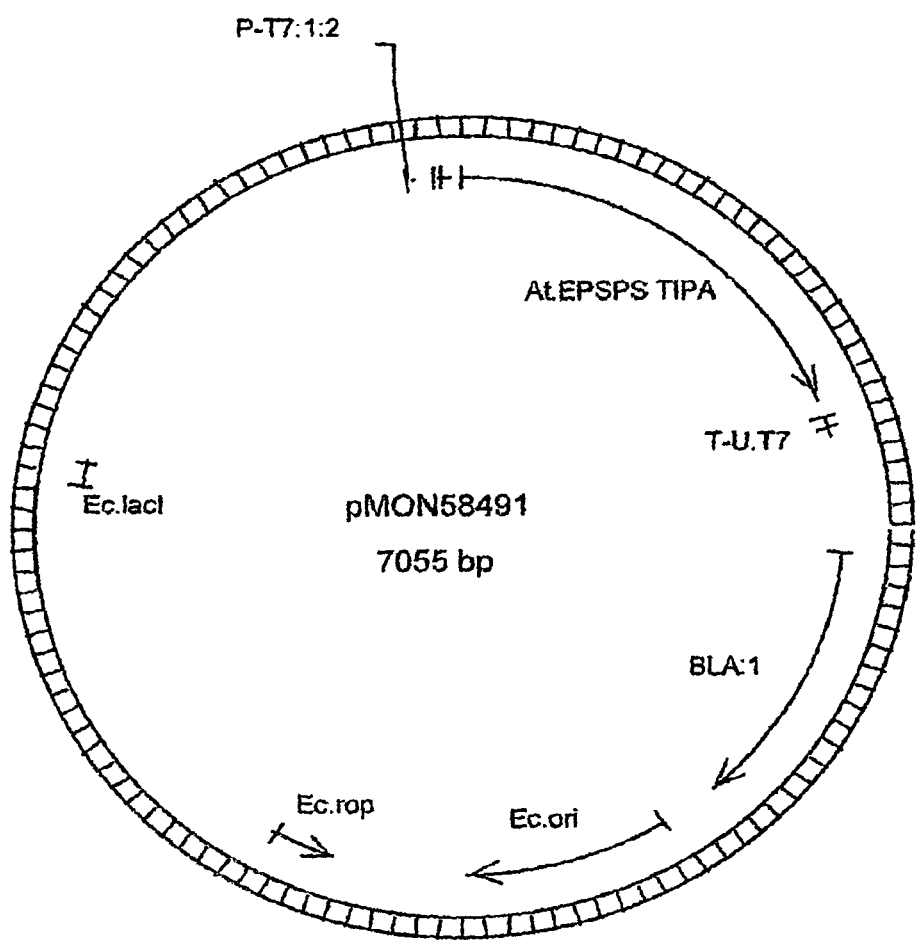
FIG. 12. DNA construct map of pMON58491 (AtTIPA variant)

The *Arabidopsis* and lettuce EPSPS TIPA variants were generated using the PCR-based QuickChange™ Site-directed Mutagenesis Kit (Stratagene Cat. No. 200518) and the DNA mutagenesis primers AtEPSPS-TIPA-F (SEQ ID NO:32) and AtEPSPS-TIPA-R (SEQ ID NO:33) for the *Ara-* bidopsis EPSPS coding sequence mutation, and LsEPSPS-TIPA-F (SEQ ID NO:34) and LsEPSPS-TIPA-R (SEQ ID NO:35) for the lettuce EPSPS coding sequence mutation and the PCR conditions were as described above. Two additional site-directed mutagenesis reactions were performed to engineer a restriction enzyme site, Nde1, at the 5' end and to remove an internal Nde1 site in the lettuce EPSPS coding sequence. The DNA fragments of the *Arabidopsis* and the lettuce EPSPS TIPA variants were then digested with Nde1 and Xho1 and cloned into a pET19 vector. The DNA molecules that encode for the variant *Arabidopsis* EPSPS and variant lettuce EPSPS are shown in SEQ ID NO:36 and SEQ ID NO:37, respectively. Examples of plant and bacterial expression DNA constructs that were made with these variant EPSPS coding sequences are illustrated in pMON81548 (LsTIPA variant, promoter of U.S. Pat. No. 6,660,911) shown in FIG. 11 and pMON58491 (AtTIPA variant) shown in FIG. 12. Any of the variant EPSPS coding sequences of the present invention can be inserted into a plant expression cassette, for example, that contained in pMON81519 or pMON81548 by replacing the existing coding sequence.

Example 2

EPSPS Purification and Enzyme Analysis

The wild type and variant EPSPS coding sequences were cloned into a pET-19b base vector (Novagen, Madison, Wis.). The plant (maize) class I EPSPS variants so created were assigned pMON plasmid numbers (Table 2). The variant EPSPS proteins were purified from the *E. coli* host using the protocols outlined in the pET system manual, 9th edition (Novagen) or by the following method. A single colony or a few microliters from a glycerol stock was inoculated into 4 mL LB medium containing 0.1 mg/mL carbenicillin antibiotic. The culture was incubated with shaking at 37 C for 4 hours. The cultures were stored at 4° C. overnight. The following morning, 1 mL of the overnight culture was used to inoculate 100 mL of fresh LB medium containing 0.1 mg/mL carbenicillin. The cultures were incubated with shaking at 37 C for 4-5 hours, then the cultures were placed at 4° C. for 5-10 minutes. The cultures were then induced with IPTG (1 mM final concentration) and incubated with shaking at 30 C for 4 hours or 20° C. overnight. The cells were harvested by centrifugation at 7000 rpm for 20 minutes at 4° C. The supernatant was removed and the cells were frozen at −70° C. until further use. The proteins were extracted by resuspending the cell pellet in BugBuster reagent (Novagen) using 5 mL reagent per gram of cells. Benzonase (125 Units) was added to the resuspension and the cell suspension was then incubated on a rotating mixer for 20 minutes at room temperature. The cell debris was removed by centrifugation at 10,000 rpm for 20 minutes at room temperature. The supernatant was passed through a 0.45 µm syringe-end filter and transferred to a fresh tube. A pre-packed columns containing 1.25 mL of His-Bind resin was equilibrated with 10 mL of 5 mM imidazole, 0.5 M NaCl, 20 mM Tris-HCl pH 7.9 (1× Binding Buffer). The column was then loaded with the prepared cell extract. After the cell extract had drained, the column was then washed with 10 mL of 1× Binding Buffer, followed with 10 mL of 60 mM imidazole, 0.5 M NaCl, 20 mM Tris-HCl pH 7.9 (1× Wash Buffer). The protein was eluted with 5 mL of 1 M imidazole, 0.5 M NaCl, 20 mM Tris-HCl pH 7.9 (1× elution buffer). Finally the protein was dialyzed into 50 mM Tris-HCl pH 6.8. The resulting protein solution was concentrated to ~0.1-0.4 mL using Ultrafree—centrifugal device (Biomax-10K MW cutoff, Millipore Corp, MA). Proteins were diluted to 10 mg/mL and 1 mg/mL in 50 mM Tris pH 6.8, 30 percent final glycerol and stored at −20° C. Protein concentration was determined using Bio-Rad protein assay (Bio-Rad Laboratories, CA). Bovine serum albumin was used to generate a standard curve 1-5 µg. Samples (10 µL) were added to wells in a 96 well-plate and mixed with 200 µL of Bio-Rad protein assay reagent (1 part dye reagent concentrate: 4 parts water). The samples were read at $OD_{595}$ after ~5 minutes using a spectraMAX 250 plate reader (Molecular Devices Corporation, Sunnyvale, Calif.) and compared to the standard curve.

The EPSPS enzyme assays contained 50 mM $K^+$-HEPES pH 7.0 and 1 mM shikimate-3-phosphate (Assay mix). The $K_m$-PEP were determined by incubating assay mix (30 µL) with enzyme (10 µL) and varying concentrations of [$^{14}C$] PEP in a total volume of 50 µL. The reactions were quenched after various times with 50 µL of 90 percent ethanol/0.1 M acetic acid pH 4.5 (quench solution). The samples were centrifuged at 14,000 revolutions per minute and the resulting supernatants were analyzed for $^{14}C$-EPSP production by HPLC. The percent conversion of $^{14}C$-PEP to $^{14}C$-EPSP was determined by HPLC radioassay using an AX100 weak anion exchange HPLC column (4.6×250 mm, SynChropak) with 0.26 M isocratic potassium phosphate eluant, pH 6.5 at 1 mL/minute mixed with Ultima-Flo AP cocktail at 3 mL/min (Packard). Initial velocities were calculated by multiplying fractional turnover per unit time by the initial concentration of the substrate.

The inhibition constant ($K_i$) were determined by incubating assay mix (30 µL) with and without glyphosate and $^{14}C$-PEP (10 µL of 2.6 mM). The reaction was initiated by the addition of enzyme (10 µL). The assay was quenched after 2 minutes with quench solution. The samples were centrifuged at 14,000 rpm and the conversion of $^{14}C$-PEP to $^{14}C$-EPSP was determined as shown above. The steady-state and $IC_{50}$ data were analyzed using the GraFit software (Erithacus Software, UK). The $K_i$ values were calculated from the $IC_{50}$ values using the following algorithm: $K_i=[IC]_{50}/(1+[S]/K_m)$. The assays were done such that the $^{14}C$-PEP to $^{14}C$-EPSP turnover was ≦30 percent. In these assays bovine serum albumin (BSA) and phosphoenolpyruvate (PEP) were obtained from Sigma. Phosphoenol-[1-$^{14}C$]pyruvate (29 mCi/mmol) was from Amersham Corp. (Piscataway, N.J.).

The maize EPSPS variants that were cloned into pET-19b and from which proteins were expressed and assayed, included the double variants TIPS, TIPT, TIPG, TIPC, TIPA, TIPV, TIPM, TIPL, and TIPI; and single variants T102I, P106S, P106T, and P106L (Table 2). The enzymes were purified and assayed for apparent $K_m$ of PEP ($K_m$-PEP) and inhibition by glyphosate ($K_i$). The TIPS variant is well known and is currently in the commercial Roundup Ready® corn product GA21 (U.S. Pat. No. 6,040,497) and its kinetic parameters serve as the baseline value for a glyphosate resistant class I EPSPS enzyme that is sufficient to provide glyphosate tolerance to a transgenic plant. All the variants were characterized and the kinetic parameters are shown in Table 2. Substantial differences were observed between these variants. Surprisingly, the results showed that two of the new variants, TIM and TIPT, were more resistant to glyphosate than the TIPS variant and demonstrated a similar $K_m$-PEP. These EPSPS enzyme double variants will provide enhanced glyphosate tolerance when appropriately expressed in transgenic plants. The variant TIPG has similar $K_m$-PEP as the wild-type enzyme (WT), but has a $K_i$ of only 38.6 µM, not an improvement over TIPS, but this $K_i$ should be sufficient to provide glyphosate tolerance in transgenic plants when appropriately expressed. The variants TIPC and TIPI show a high level of resistance to glyphosate but have 1.7-fold and 2.2-fold higher $K_m$-PEP than the wild-type enzyme, respectively. Although TIPC and TIPI are somewhat less efficient than the wild-type enzyme for $K_m$-PEP, they do show a high level of resistance to glyphosate and when these are overexpressed as a transgene in plant cells, these enzymes should be sufficient to provide glyphosate tolerance. Other double variants that include TIPV, TIPM, TIPL showed very high resistance to glyphosate, but have significantly higher $K_m$ for PEP and therefore do not have sufficient substrate binding activity to provide useful EPSPS enzyme activity to a transgenic plant. Additional double variants TIPD and TIPN had a $K_m$ for PEP of 355 and 566, respectively and were not assayed for $K_i$ for glyphosate because the substrate binding activity was too inefficient for these variants to have effective EPSPS activity. For comparison purposes, the enzyme kinetics of the naturally occurring class II glyphosate resistant EPSPS isolated from *Agrobacterium* strain CP4 (CP4 EPSPS) was expressed from pMON21104 (RecA promoter/G10 leader/CP4 EPSPS/T7 terminator) and assayed under the same conditions as the maize variant EPSPSs and demonstrated a $K_m$-PEP of 14.4 μM and $K_i$ for glyphosate of 5100 μM.

TABLE 2

Steady-state kinetic parameters of maize EPSPS variants

| pMON# EPSPS variant | $K_m$-PEP (μM) | $K_i$-glyp (μM) |
|---|---|---|
| pMON70461 WT | 27 ± 4 | 0.50 ± 0.06 |
| PMON70462 TIPS | 10.6 ± 1.6 | 58.0 ± 14 |
| PMON58452 TIPT | 11.2 ± 1.8 | 101.3 ± 12.7 |
| PMON42480 TIPG | 23.0 ± 3.7 | 38.6 ± 1.7 |
| PMON42485 TIPC | 47.0 ± 4.0 | 818.2 ± 74.4 |
| PMON42481 TIPA | 10.2 ± 1.1 | 148.3 ± 18.3 |
| PMON42486 TIPI | 60.3 ± 2.8 | 2500 ± 900 |
| pMON42482 TIPV | 109.3 ± 12.9 | 1600 ± 400 |
| pMON42484 TIPM | 143.3 ± 12.6 | 37200 ± 1500 |
| pMON42483 TIPL | 99.5 ± 8.9 | 2100 ± 100 |
| pMON58455 T102I | 233.0 ± 25.5 | 148.6 ± 12.4 |
| pMON70466 P106S | 17.1 ± 2.8 | 1.0 ± 0.1 |
| pMON70467 P106T | 24.6 ± 4.4 | 4.0 ± 0.6 |
| pMON58451 P106L | 86.7 ± 5.7 | 28.6 ± 0.1 |
| pMON21104 CP4 EPSPS | 14.4 ± 2.4 | 5100 ± 0.1 |

Example 3

Figure 6:
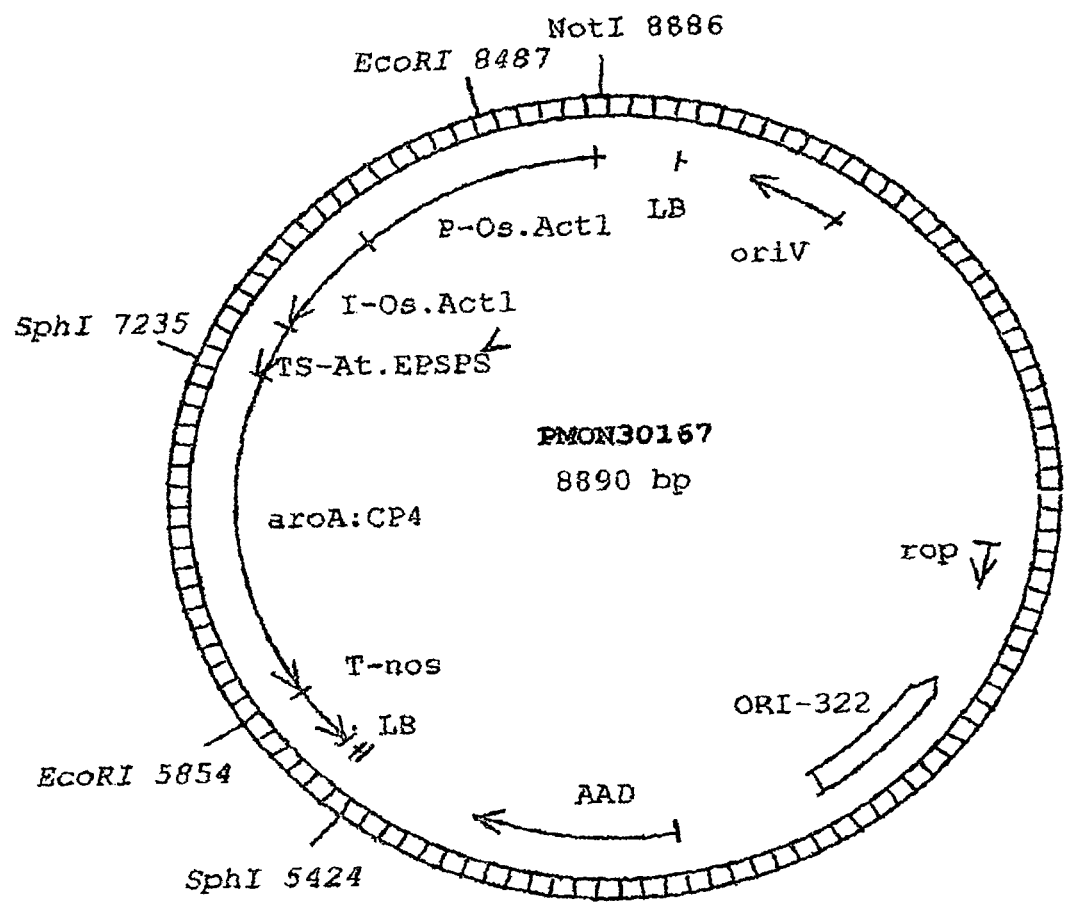
FIG. 6. DNA construct map of pMON30167 (CP4 EPSPS)
Figure 7:
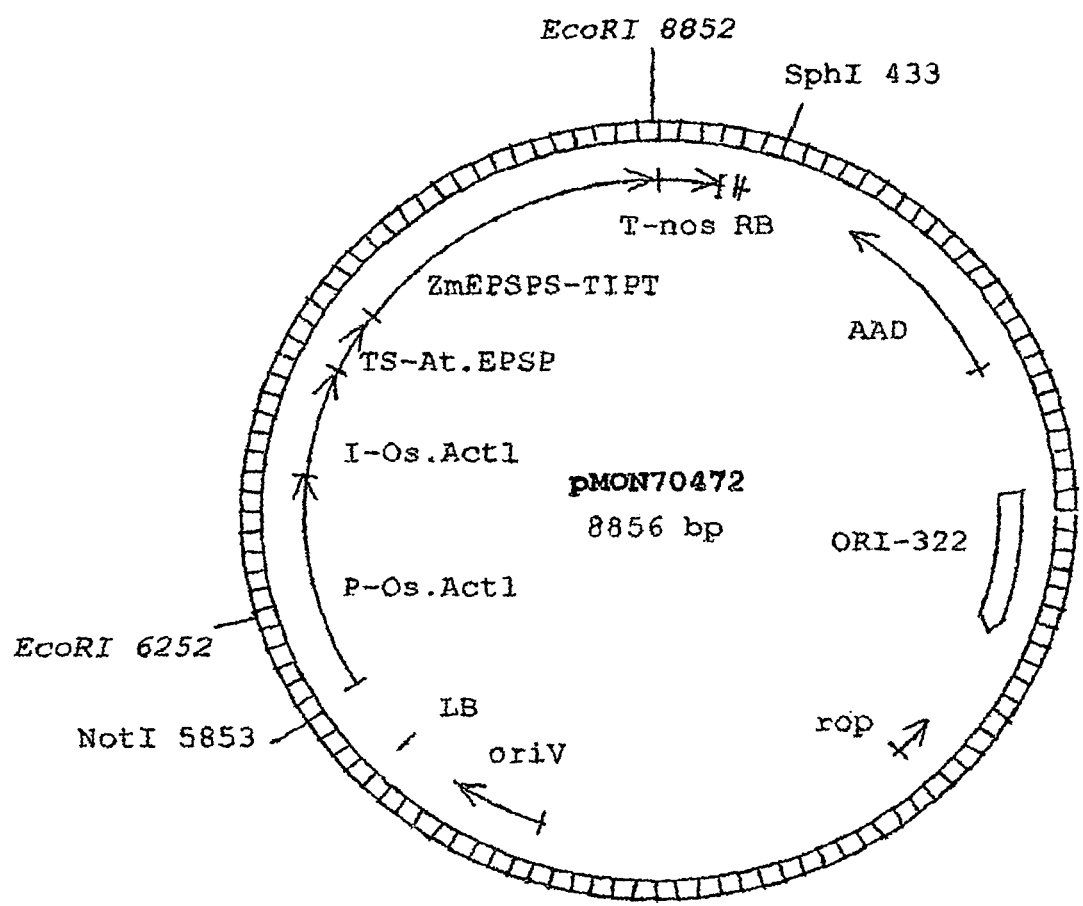
FIG. 7. DNA construct map of pMON70472 (ZmTIPT variant)
Figure 8:
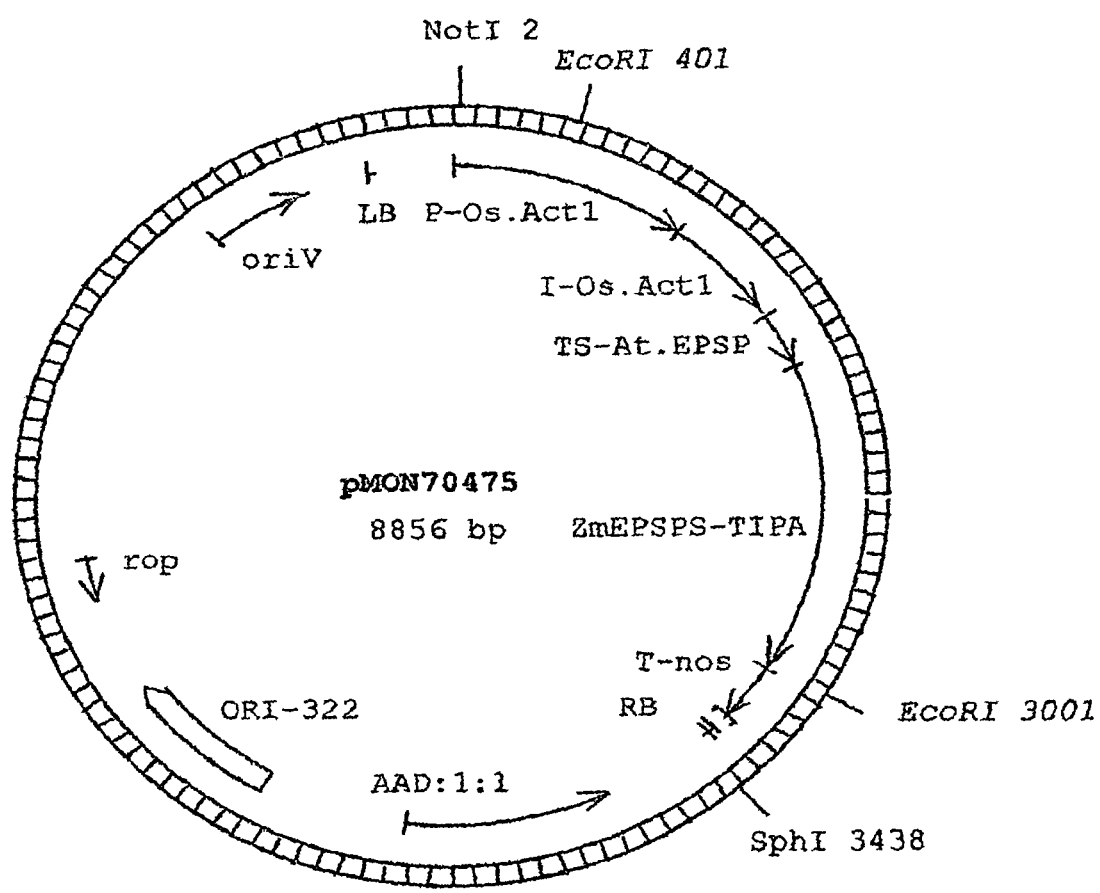
FIG. 8. DNA construct map of pMON70475 (ZmTIPA variant)

The maize EPSPS double variants ZmTIPT (SEQ ID NO:38) and ZmTIPA (SEQ ID NO:39) were made with as a CTP translational fusion into plant expression DNA constructs, pMON70472 (FIG. 7) and pMON70475 (FIG. 8), respectively. pMON30167 (FIG. 6) was digested with SphI/NotI and EcoRI, a Not I/Eco RI backbone DNA fragment of pMON30167 and a Sph I/Not I DNA fragment (rice actin promoter, P-OsAct1 and intron, I-Os.Act1, U.S. Pat. No. 5,641,876) were gel purified. A maize EPSPS-TIPT DNA molecule was isolated from pMON58452 by incorporating Sph I and Eco RI endonuclease sites in the ends with DNA primer molecules ZmAroA-1 (SEQ ID NO:40) and ZmAroA-2 (SEQ ID NO:41). The amplified mEPSPS-TIPT DNA fragment was digested with SphI and Eco RI and gel purified. A triple ligation was performed with the two pMON30167 fragments and the modified maize EPSPS-TIPT DNA fragment. The ligated plasmid was transformed into *E. coli* strain XL1-blue following the manufacturer's instruction and screened for colonies with the correct plasmid. The mature maize EPSPS N-terminus was restored (should be Ala not Met) by mutagenesis with Stratagene QuikChange kit according to manufacturer's instruction and using DNA primer molecules ZmAroA-3 (SEQ ID NO:42) and ZmAroA-4 (SEQ ID NO:43) contained in pMON70472 (FIG. 7).

Example 4

A DNA construct containing the TIPT variant (pMON70472, FIG. 7) under the control of rice actin promoter was transformed into corn plant cells (LH198 x Hill) by an *Agrobacterium* mediated transformation method. For example, a disarmed *Agrobacterium* strain C58 harboring the binary DNA construct of the present invention is used. The DNA construct is transferred into *Agrobacterium* by a triparental mating method (Ditta et al., Proc. Natl. Acad. Sci. 77:7347-7351, 1980). Liquid cultures of *Agrobacterium* are initiated from glycerol stocks or from a freshly streaked plate and grown overnight at 26° C.-28° C. with shaking (approximately 150 rpm) to mid-log growth phase in liquid LB medium, pH 7.0 containing the appropriate antibiotics. The *Agrobacterium* cells are resuspended in the inoculation medium (liquid CM4C) and the density is adjusted to $OD_{660}$ of 1. Freshly isolated Type II immature HiIIxLH198 and HiII corn embryos are inoculated with *Agrobacterium* containing a construct and co-cultured several days in the dark at 23° C. The embryos are then transferred to delay media and incubated at 28° C. for several or more days. All subsequent cultures are kept at this temperature. The embryos are transferred to a first selection medium containing carbenicillin 500/0.5 mM glyphosate). Two weeks later, surviving tissue are transferred to a second selection medium containing carbenicillin 500/1.0 mM glyphosate). Subculture surviving callus every 2 weeks until events can be identified. This may take about 3 subcultures on 1.0 mM glyphosate. Once events are identified, bulk up the tissue to regenerate. The plantlets (events) are transferred to MSOD media in culture vessel and kept for two weeks. The transformation efficiency is determined by dividing the number of events produced by the number of embryos inoculated. Then the plants with roots are transferred into soil. Those skilled in the art of monocot transformation methods can modify this method to provide substantially identical transgenic monocot plants containing the DNA compositions of the present invention, or use other methods, such as, particle gun, that are known to provide transgenic monocot plants.

The results of molecular analysis and glyphosate selection of the regenerated corn events transformed with a DNA construct containing ZmTIPT are shown in Table 3. The events were analyzed for single copy insertion in the corn genome and for vegetative and male fertility. Eight of the thirteen transgenic events (61%) containing the pMON70472 (TIPT) plant expression cassette were assayed using Taqman® analysis (ABI, Foster City, Calif.) and determined to be a single copy insert into the corn genome. The events were treated with a foliar application of 32 oz/acre of Roundup® Ultra at the V4 stage of corn development and then another foliar application of 64 oz/acre Roundup® Ultra at about V7. The treated plants were scored for vegetative (glypT) and reproductive tolerance (fertile) to glyphosate. Four of the eight single copy events (50%) showed no vegetative injury due to the glyphosate application at V4 (% V4 glypT). A 64 oz Roundup® Ultra treatment was applied at around the V7 stage and the plants were scored for vegetative glyphosate tolerance and male fertility (% V7glypT/fertile). All four of the events 100% (4/4) that were single copy and vegetatively tolerant to glyphosate at V4 were also vegetatively tolerant and fully male fertile after the V7 treatment. Compared to the commercial standard glyphosate resistant EPSPS(CP4 EPSPS) the ZmTIPT variant performed surprisingly well.

DNA constructs containing the TIPT variant of a class I EPSPS provide plants that are vegetatively and reproductively tolerant to a glyphosate containing herbicide.

TABLE 3

Results of glyphosate tolerance treatment of corn events containing the TIPT EPSPS variant.

| DNA Construct | #events | single copy | % V4 glypT | % V7 glypT/fertile |
|---|---|---|---|---|
| pMON70472 (ZmTIPT) | 13 | 61% (8/13) | 50% (4/8) | 100% (4/4) |
| pMON30167 (CP4 EPSPS) | 24 | 33% (8/24) | 62% (5/8) | 100% (5/5) |

Example 5

Figure 10:
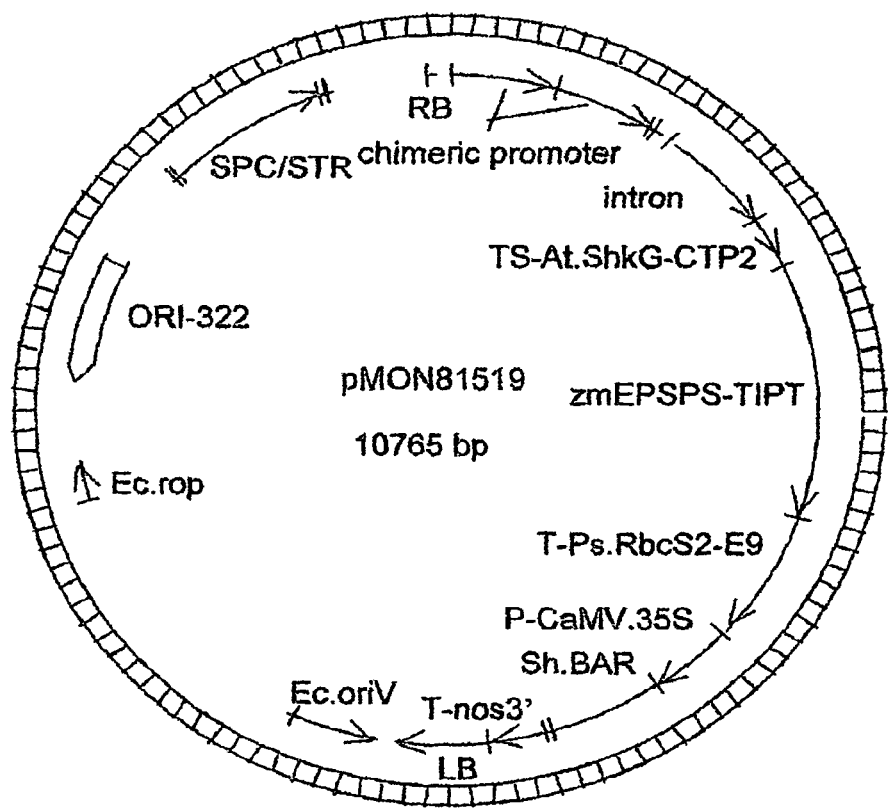
FIG. 10. DNA construct map of pMON81519 (ZmTIPT variant)

The ZmTIPT variant was constructed into a plant expression construct suitable for dicot plant expression. The DNA construct was designated pMON81519 and is illustrated in FIG. 10. The DNA construct and control constructs were transferred into *Agrobacterium* by a triparental mating method as previously described. The transformed *Agrobacterium* cells were used to transfer the plant expression cassette into *Arabidopsis* and tobacco cells.

*Arabidopsis* embryos were transformed by an *Agrobacterium* mediated method essentially as described by Bechtold N, et al., CR Acad Sci Paris Sciences di la vie/life sciences 316: 1194-1199, (1993). An *Agrobacterium* strain ABI containing a DNA construct is prepared as inoculum by growing in a culture tube containing 10 mls Luria Broth and antibiotics. The *Agrobacterium* inoculum is pelleted by centrifugation and resuspended in 25 ml Infiltration Medium (MS Basal Salts 0.5%, Gamborg's B-5 Vitamins 1%, Sucrose 5%, MES 0.5 g/L, pH 5.7) with 0.44 nM benzylaminopurine (10 ul of a 1.0 mg/L stock in DMSO per liter) and 0.02% Silwet L-77 to an $OD_{600}$ of 0.6.

Mature flowering *Arabidopsis* plants are vacuum infiltrated in a vacuum chamber with the *Agrobacterium* inoculum by inverting the pots containing the plants into the inoculum. The chamber is sealed, a vacuum is applied for several minutes, release the vacuum suddenly, blot the pots to remove excess inoculum, cover pots with plastic domes and place pots in a growth chamber at 21° C. 16 hours light and 70% humidity. Approximately 2 weeks after vacuum infiltration of the inoculum, cover each plant with a Lawson 511 pollination bag. Approximately 4 weeks post infiltration, withhold water from the plants to permit dry down. Harvest seed approximately 2 weeks after dry down.

The transgenic *Arabidopsis* plants produced by the infiltrated seed embryos are selected from the nontransgenic plants by a germination selection method. The harvested seed is surface sterilized then spread onto the surface of selection media plates containing MS Basal Salts 4.3 g/L, Gamborg's B-5 (500×) 2.0 g/L, MES 0.5 g/L, and 8 g/L Phytagar with Carbenicillin 250 mg/L, Cefotaxime 100 mg/L, and PPM 2 ml/L and 300 µM glyphosate added as a filter sterilized liquid solution, after autoclaving. The pMON81519 V1 events and control construct pMON81517 glyphosate tolerant transgenic *Arabidopsis* plants are selected by spray application of glyphosate herbicide at a rate of 24 ounces/acre, the surviving plants are transplanted into individual pots. The V1 plants are sprayed a second time corresponding to the observation of bolting, approximately 16 days after the at a rate of 24 ounces/acre. The second spray will determine the efficacy of the two constructs for conferring reproductive tolerance. The plants are observed for vegetative and reproductive effects of glyphosate application. Sixty-two plants were assayed that were transformed with the control construct pMON81517 that contains the CP4 EPSPS (class II EPSPS) coding sequence, forty-nine plants were assayed that were transformed with pMON81519. The results shown in Table 4 demonstrate that the percentage of plants showing glyphosate tolerance and fertility is about the same for the ZmTIPT class I EPSPS variant as for the class II EPSPS.

Tobacco is a well known model plant for testing of transgene constructs and the methods of transformation are well known in the art of plant transformation. Briefly, tobacco leaf tissue is cut and placed onto solid pre-culture plates containing the appropriate culture medium. The day before *Agrobacterium* inoculation, a 10 µl loop of a transformed *Agrobacterium* culture containing pMON81519 or control construct is placed into a tube containing 10 mls of YEP media with appropriate antibiotics to maintain selection of the DNA construct. The tube is put into a shaker to grow overnight at 28° C. The $OD_{600}$ of the *Agrobacterium* is adjusted to 0.15-0.30 $OD_{600}$ with TXD medium. Inoculate tobacco leaf tissue explants by pipetting 7-8 mls of the liquid *Agrobacterium* suspension directly onto the pre-culture plates covering the explant tissue. Allow the *Agrobacterium* to remain on the plate for 15 minutes. Tilt the plates and aspirate liquid off using a sterile 10 ml wide bore pipette. The explants are co-cultured on these same plates for 2-3 days. The explants are then transferred to fresh medium containing appropriate selection agents and maintained for 3-4 weeks at which time the callus tissue is transferred to fresh medium. At 6-8 weeks, shoots should be excised from the callus allowed to root in culture media. Rooted shoots are then transferred to soil after 2-3 weeks. The plants are treated with 16-24 oz/Acre glyphosate and scored for vegetative and reproductive tolerance. The results shown in Table 4 demonstrate that the percentage of plants showing glyphosate tolerance and fertility is about the same for the ZmTIPT class I EPSPS variant as for the class II EPSPS.

TABLE 4

Results of glyphosate tolerance treatment of *Arabidopsis* and tobacco events containing the TIPT EPSPS variant.

| DNA Construct | Tobacco % glypT/fertile | *Arabidopsis* % glypT/fertile |
|---|---|---|
| PMON81517 (CP4 EPSPS) | 56% (N = 41) | 61% (N = 62) |
| PMON81519 (ZmTIPT) | 49% (N = 39) | 65% (N = 49) |

Example 6

Class I EPSPSs can be modified by site-directed mutagenesis methods or random mutagenesis method to provide an enzyme that is resistant to glyphosate. The present invention preferably provides amino acid substitutions of the Thr102 and Pro106 positions. In addition to the previously described TIP-T,G,C,A, and I variants of the present invention, an additional substitution was performed of the Thr102 codon was replaced with a leucine (L, Leu) codon and the Pro106 codon was replaced with an alanine (A, Ala) codon by site-directed modification of the corresponding codons in a maize EPSPS DNA coding sequence resulting in a variant ZmTLPA (SEQ ID NO:44) that provides a glyphosate resistant enzyme. In another variant, the Thr102 codon was replaced with a codon for Glutamine (Q, Gln), the Pro106 codon modified to an Ala codon, resulting in a TQPA variant.

These maize EPSPS variants, TLPA and TQPA were generated using the PCR-based QuickChange™ Site-directed Mutagenesis Kit by Stratagene (Cat. No. 200518). The unmodified maize EPSPS coding sequence was used as the template for PCR to generate the variants. The mutagenesis oligo primers were ordered from Invitrogen. The PCR was set up in a 50 µl reaction in the following manner: dH$_2$O 38 µl; 2 mM dNTP 1 µL; 10× buffer 5 µL; pMON70461 1 µL (10 ng); ZmTLPA-1 (SEQ ID NO:45) 2 µL; ZmTLPA-2 (SEQ ID NO:46) 2 µL; pfu Turbo enzyme 1 µL. The PCR was carried out on a MJ Research PTC-200 thermal cycler using the following program: Step 1—94° C. for 2'; Step 2—94° C. for 30"; Step 3—55° C. for 30"; Step 4—68° C. for 14'; Step 5—go to step 2, 16 times; Step 6—End. At the end of the PCR, 1 µl of the restriction enzyme DpnI was added to each 50 µl of PCR reaction and the mixture was incubated at 37° C. for 1 hour. After the DpnI treatment, 1 µl of the treated reaction mixture was used to transform the competent *E. coli* strain XL1-blue strain (Stratagene) following the manufacturer's instruction. The transformed cells were plated on a Petri dish containing carbenicillin at a final concentration of 0.1 mg/mL. The plate was then incubated at 37° C. overnight. Single colonies were picked the next day and used to inoculate a 3 mL liquid culture containing 0.1 mg/mL carbenicillin. The liquid culture was incubated overnight at 37° C. with agitation at 250 rpm. Plasmid DNA was prepared from 1 mL of the liquid culture using Qiagen's miniprep Kit (Cat. No. 27160). The DNA was eluted in 50 µl of dH$_2$O. The entire coding region of three independent clones from each mutagenesis was sequenced and confirmed to contain the desired mutation. The variant coding sequences were inserted into a pET19 expression vector in the proper orientation to provide expression of the variant enzyme as a translational fusion with a purification tag.

The mutant maize EPSPS enzymes (TLPA and TQPA) were assayed for catalytic activity, substrate binding, and resistance to glyphosate ($K_i$) using the assay conditions previously described. The results are shown in Table 5. These mutants were compared to the wild type (WT) unmodified maize EPSPS, and the TIPA variant. The results provide evidence that the TLPA variant is resistant to glyphosate and has sufficient enzyme kinetics that when expressed in a transgenic plant will provide glyphosate tolerance to the transgenic plant when fused with a CTP or modified for chloroplast expression. Further amino acid substitutions at the 106 position that include threonine, glycine, cysteine and isoleucine are expected to result in a glyphosate resistant enzyme as observed in combination with the T-I modification at position 102.

TABLE 5

| | EPSPS steady-state kinetics | | | |
|---|---|---|---|---|
| Enzyme | $k_{cat}$ (s$^{-1}$) | $K_m$-PEP (□M) | $k_{cat}/K_m$ (□M$^{-1}$s$^{-1}$) | Ki (□M) |
| WT maize | 8.8 ± 0.5 | 27 ± 4 | 0.3 | 0.5 ± 0.06 |
| TIPA | 2.1 ± 0.1 | 10.2 ± 1.1 | 0.2 | 148.3 ± 18.3 |
| TLPA | 2.4 ± 0.1 | 13.1 ± 2.5 | 0.2 | 46.8 ± 7.6 |
| TQPA | 3.8 ± 0.2 | 163.8 ± 22.9 | 0.02 | 2200 ± 200 |

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

SEQUENCE LISTING

```
<160> NUMBER OF SEQ ID NOS: 52

<210> SEQ ID NO 1
<211> LENGTH: 6
<212> TYPE: PRT
<213> ORGANISM: Artificial sequence
<220> FEATURE:
<223> OTHER INFORMATION: peptide motif of class I EPSPS
<220> FEATURE:
<221> NAME/KEY: MISC_FEATURE
<222> LOCATION: (3)..(4)
<223> OTHER INFORMATION: Xaa is any amino acid

<400> SEQUENCE: 1

Gly Thr Xaa Xaa Arg Pro
1               5

<210> SEQ ID NO 2
<211> LENGTH: 6
<212> TYPE: PRT
<213> ORGANISM: Artificial sequence
<220> FEATURE:
```

-continued

<223> OTHER INFORMATION: variant EPSPS substrate binding domain
<220> FEATURE:
<221> NAME/KEY: MISC_FEATURE
<222> LOCATION: (2)..(2)
<223> OTHER INFORMATION: Xaa is Isoleucine or Leucine
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Thr, Gly, Cys, Ala, Ile

<400> SEQUENCE: 2

Gly Xaa Xaa Xaa Arg Xaa
1               5

<210> SEQ ID NO 3
<211> LENGTH: 1335
<212> TYPE: DNA
<213> ORGANISM: Zea Mays
<220> FEATURE:
<223> OTHER INFORMATION: EPSPS gene

<400> SEQUENCE: 3

```
atggcgggtg ccgaagaaat cgtgctgcag ccgatcaagg agatctccgg caccgtcaag        60
ctgccggggt ccaagtcgct ttccaaccgg atcctcctac tcgccgccct gtccgagggg       120
acaacagtgg ttgataacct gctgaacagt gaggatgtcc actacatgct cggggccttg       180
aggactcttg gtctctctgt cgaagcggac aaagctgcca aaagagctgt agttgttggc       240
tgtggtggaa agttcccagt tgaggatgct aaagaggaag tgcagctctt cttggggaat       300
gctggaactg caatgcggcc attgacagca gctgttactg ctgctggtgg aaatgcaact       360
tacgtgcttg atggagtacc aagaatgagg gagagaccca ttggcgactt ggttgtcgga       420
ttgaagcagc ttggtgcaga tgttgattgt ttccttggca ctgactgccc acctgttcgt       480
gtcaatggaa tcggagggct acctggtggc aaggtcaagc tgtctggctc catcagcagt       540
cagtacttga gtgccttgct gatggctgct ccttttggct tggggatgt ggagattgaa       600
atcattgata aattaatctc cattccgtac gtcgaaatga cattgagatt gatggagcgt       660
tttggtgtga agcagagca ttctgatagc tgggacagat tctacattaa gggaggtcaa       720
aaatacaagt cccctaaaaa tgcctatgtt gaaggtgatg cctcaagcgc aagctatttc       780
ttggctggtg ctgcaattac tggagggact gtgactgtgg aaggttgtgg caccaccagt       840
ttgcagggtg atgtgaagtt tgctgaggta ctggagatga tgggagcgaa ggttacatgg       900
accgagacta gcgtaactgt tactggccca ccgcgggagc catttgggag gaaacacctc       960
aaggcgattg atgtcaacat gaacaagatg cctgatgtcg ccatgactct tgctgtggtt      1020
gccctctttg ccgatggccc gacagccatc agagacgtgg cttcctggag agtaaaggag      1080
accgagagga tggttgcgat ccggacggag ctaaccaagc tgggagcatc tgttgaggaa      1140
gggccggact actgcatcat cacgccgccg gagaagctga acgtgacggc gatcgacacg      1200
tacgacgacc acaggatggc gatggccttc tcccttgccg cctgtgccga ggtccccgtc      1260
accatccggg accctgggtg cacccggaag accttccccg actacttcga tgtgctgagc      1320
actttcgtca agaat                                                      1335
```

<210> SEQ ID NO 4
<211> LENGTH: 51
<212> TYPE: DNA
<213> ORGANISM: Artificial sequence

```
<220> FEATURE:
<223> OTHER INFORMATION: mutagenesis primer

<400> SEQUENCE: 4
cttcttgggg aatgctggaa ttgcaatgcg gtcattgaca gcagctgtta c       51

<210> SEQ ID NO 5
<211> LENGTH: 51
<212> TYPE: DNA
<213> ORGANISM: Artificial sequence
<220> FEATURE:
<223> OTHER INFORMATION: mutagenesis primer

<400> SEQUENCE: 5
gtaacagctg ctgtcaatga ccgcattgca attccagcat tccccaagaa g       51

<210> SEQ ID NO 6
<211> LENGTH: 22
<212> TYPE: DNA
<213> ORGANISM: Artificial sequence
<220> FEATURE:
<223> OTHER INFORMATION: mutagenesis primer

<400> SEQUENCE: 6
ggaatgctgg aattgcaatg cg                                       22

<210> SEQ ID NO 7
<211> LENGTH: 22
<212> TYPE: DNA
<213> ORGANISM: Artificial sequence
<220> FEATURE:
<223> OTHER INFORMATION: mutagenesis primer

<400> SEQUENCE: 7
cgcattgcaa ttccagcatt cc                                       22

<210> SEQ ID NO 8
<211> LENGTH: 38
<212> TYPE: DNA
<213> ORGANISM: Artificial sequence
<220> FEATURE:
<223> OTHER INFORMATION: mutagenesis primer

<400> SEQUENCE: 8
gctggaactg caatgcggac attgacagca gctgttac                      38

<210> SEQ ID NO 9
<211> LENGTH: 38
<212> TYPE: DNA
<213> ORGANISM: Artificial sequence
<220> FEATURE:
<223> OTHER INFORMATION: mutagenesis primer

<400> SEQUENCE: 9
gtaacagctg ctgtcaatgt ccgcattgca gttccagc                      38

<210> SEQ ID NO 10
<211> LENGTH: 38
<212> TYPE: DNA
<213> ORGANISM: Artificial sequence
<220> FEATURE:
<223> OTHER INFORMATION: mutagenesis primer

<400> SEQUENCE: 10
gctggaactg caatgcggtc attgacagca gctgttac                      38
```

```
<210> SEQ ID NO 11
<211> LENGTH: 38
<212> TYPE: DNA
<213> ORGANISM: Artificial sequence
<220> FEATURE:
<223> OTHER INFORMATION: mutagenesis primer

<400> SEQUENCE: 11
gtaacagctg ctgtcaatga ccgcattgca gttccagc                           38

<210> SEQ ID NO 12
<211> LENGTH: 22
<212> TYPE: DNA
<213> ORGANISM: Artificial sequence
<220> FEATURE:
<223> OTHER INFORMATION: mutagenesis primer

<400> SEQUENCE: 12
caatgcggct attgacagca gc                                            22

<210> SEQ ID NO 13
<211> LENGTH: 22
<212> TYPE: DNA
<213> ORGANISM: Artificial sequence
<220> FEATURE:
<223> OTHER INFORMATION: mutagenesis primer

<400> SEQUENCE: 13
gctgctgtca atagccgcat tg                                            22

<210> SEQ ID NO 14
<211> LENGTH: 22
<212> TYPE: DNA
<213> ORGANISM: Artificial sequence
<220> FEATURE:
<223> OTHER INFORMATION: mutagenesis primer

<400> SEQUENCE: 14
gcaatgcggg gattgacagc ag                                            22

<210> SEQ ID NO 15
<211> LENGTH: 22
<212> TYPE: DNA
<213> ORGANISM: Artificial sequence
<220> FEATURE:
<223> OTHER INFORMATION: mutagenesis primer

<400> SEQUENCE: 15
ctgctgtcaa tccccgcatt gc                                            22

<210> SEQ ID NO 16
<211> LENGTH: 22
<212> TYPE: DNA
<213> ORGANISM: Artificial sequence
<220> FEATURE:
<223> OTHER INFORMATION: mutagenesis primer

<400> SEQUENCE: 16
gcaatgcggg cattgacagc ag                                            22

<210> SEQ ID NO 17
<211> LENGTH: 22
<212> TYPE: DNA
<213> ORGANISM: Artificial sequence
<220> FEATURE:
<223> OTHER INFORMATION: mutagenesis primer

<400> SEQUENCE: 17
```
ctgctgtcaa tgcccgcatt gc                                          22

<210> SEQ ID NO 18
<211> LENGTH: 22
<212> TYPE: DNA
<213> ORGANISM: Artificial sequence
<220> FEATURE:
<223> OTHER INFORMATION: mutagenesis primer

<400> SEQUENCE: 18
gcaatgcggg tattgacagc ag                                          22

<210> SEQ ID NO 19
<211> LENGTH: 22
<212> TYPE: DNA
<213> ORGANISM: Artificial sequence
<220> FEATURE:
<223> OTHER INFORMATION: mutagenesis primer

<400> SEQUENCE: 19
ctgctgtcaa tacccgcatt gc                                          22

<210> SEQ ID NO 20
<211> LENGTH: 25
<212> TYPE: DNA
<213> ORGANISM: Artificial sequence
<220> FEATURE:
<223> OTHER INFORMATION: mutagenesis primer

<400> SEQUENCE: 20
gcaatgcggc tgttgacagc agctg                                       25

<210> SEQ ID NO 21
<211> LENGTH: 25
<212> TYPE: DNA
<213> ORGANISM: Artificial sequence
<220> FEATURE:
<223> OTHER INFORMATION: mutagenesis primer

<400> SEQUENCE: 21
cagctgctgt caacagccgc attgc                                       25

<210> SEQ ID NO 22
<211> LENGTH: 23
<212> TYPE: DNA
<213> ORGANISM: Artificial sequence
<220> FEATURE:
<223> OTHER INFORMATION: mutagenesis primer

<400> SEQUENCE: 22
gcaatgcgga tcttgacagc agc                                         23

<210> SEQ ID NO 23
<211> LENGTH: 23
<212> TYPE: DNA
<213> ORGANISM: Artificial sequence
<220> FEATURE:
<223> OTHER INFORMATION: mutagenesis primer

<400> SEQUENCE: 23
gctgctgtca agatccgcat tgc                                         23

<210> SEQ ID NO 24
<211> LENGTH: 23
<212> TYPE: DNA
<213> ORGANISM: Artificial sequence

```
<220> FEATURE:
<223> OTHER INFORMATION: mutagenesis primer

<400> SEQUENCE: 24
gcaatgcgga tgttgacagc agc                                           23

<210> SEQ ID NO 25
<211> LENGTH: 23
<212> TYPE: DNA
<213> ORGANISM: Artificial sequence
<220> FEATURE:
<223> OTHER INFORMATION: mutagenesis primer

<400> SEQUENCE: 25
gctgctgtca acatccgcat tgc                                           23

<210> SEQ ID NO 26
<211> LENGTH: 25
<212> TYPE: DNA
<213> ORGANISM: Artificial sequence
<220> FEATURE:
<223> OTHER INFORMATION: mutagenesis primer

<400> SEQUENCE: 26
gcaatgcggt gtttgacagc agctg                                         25

<210> SEQ ID NO 27
<211> LENGTH: 25
<212> TYPE: DNA
<213> ORGANISM: Artificial sequence
<220> FEATURE:
<223> OTHER INFORMATION: mutagenesis primer

<400> SEQUENCE: 27
cagctgctgt caaacaccgc attgc                                         25

<210> SEQ ID NO 28
<211> LENGTH: 38
<212> TYPE: DNA
<213> ORGANISM: Artificial sequence
<220> FEATURE:
<223> OTHER INFORMATION: DNA primer

<400> SEQUENCE: 28
caacatatgg agaaagcttc ggagattgtg cttcaacc                           38

<210> SEQ ID NO 29
<211> LENGTH: 33
<212> TYPE: DNA
<213> ORGANISM: Artificial sequence
<220> FEATURE:
<223> OTHER INFORMATION: DNA primer

<400> SEQUENCE: 29
caactcgagt taatgctttg tgattctttc aag                                33

<210> SEQ ID NO 30
<211> LENGTH: 29
<212> TYPE: DNA
<213> ORGANISM: Artificial sequence
<220> FEATURE:
<223> OTHER INFORMATION: DNA primer

<400> SEQUENCE: 30
gcatgcagaa gccttccaca gcaccggag                                     29
```

```
<210> SEQ ID NO 31
<211> LENGTH: 37
<212> TYPE: DNA
<213> ORGANISM: Artificial sequence
<220> FEATURE:
<223> OTHER INFORMATION: DNA primer

<400> SEQUENCE: 31
tctagactcg agtcagtgct tagcaaacct ctgaagc                               37

<210> SEQ ID NO 32
<211> LENGTH: 30
<212> TYPE: DNA
<213> ORGANISM: Artificial sequence
<220> FEATURE:
<223> OTHER INFORMATION: mutagenesis primer

<400> SEQUENCE: 32
aatgcaggaa tcgcaatgcg tgcacttacc                                      30

<210> SEQ ID NO 33
<211> LENGTH: 30
<212> TYPE: DNA
<213> ORGANISM: Artificial sequence
<220> FEATURE:
<223> OTHER INFORMATION: mutagenesis primer

<400> SEQUENCE: 33
ggtaagtgca cgcattgcga ttcctgcatt                                      30

<210> SEQ ID NO 34
<211> LENGTH: 29
<212> TYPE: DNA
<213> ORGANISM: Artificial sequence
<220> FEATURE:
<223> OTHER INFORMATION: mutagenesis primer

<400> SEQUENCE: 34
gcaggaatcg ctatgcgtgc attgactgc                                       29

<210> SEQ ID NO 35
<211> LENGTH: 29
<212> TYPE: DNA
<213> ORGANISM: Artificial sequence
<220> FEATURE:
<223> OTHER INFORMATION: mutagenesis primer

<400> SEQUENCE: 35
gcagtcaatg cacgcatagc gattcctgc                                       29

<210> SEQ ID NO 36
<211> LENGTH: 1340
<212> TYPE: DNA
<213> ORGANISM: Artificial sequence
<220> FEATURE:
<223> OTHER INFORMATION: variant TIPA EPSPS derived from Arabidopsis

<400> SEQUENCE: 36
tggagaaagc ttcggagatt gtgcttcaac ccattagaga atctcgggt ctcattaagc       60 ttcctggctc caagtctctc tctaatcgaa ttctgcttct cgctgctcta tctgagggaa    120
ctactgtagt ggacaacttg ttgaacagtg atgcatcaa ttcatgctt gatgcgttga      180 agatattggg acttaatgtg gaaactcaca gtgaaaacaa tcgtgctgta gttgaaggat    240
gtggcggggt atttccagct tccattgatt ccaagagtga tatcgaactt tacctcggca    300
atgcaggaat cgcaatgcgt gcacttaccg ccgcagttac tgctgcaggt ggcaacgcaa    360
```

```
gttatgtcct tgatggggtg cctcggatga gagagagacc tataggggat ttggttgttg      420
gtcttaagca gcttggtgct gatgttgaat gtactcttgg cactaactgc cctcctgttc      480
gtgtcaacgc taatggtggc cttcctggtg aaaggtgaa gctttctgga tctattagta       540
gtcagtactt gaccgctctg ctcatggcag ctcccttagc tcttggagac gtcgaaattg      600
aaattgtcga taaattgatt tctgttccgt atgttgaaat gacattgaag ttgatggaac      660
gttttggggt aagtgctgag catagtgaaa gctgggatcg tttctttgtt aagggtgggc      720
aaaaatacaa gtcgccgggt aatgcttacg tagaaggtga tgcttctagt gctagttatt      780
tcctggctgg tgctgccatt accggtgaaa ctgtcactgt tgaaggttgt ggaacgacca      840
gtttgcaggg agatgtgaaa tttgccgagg ttcttgagaa atgggatgt aaagtgtcct       900 ggacagagaa cagtgtgact gtgacagggc cgtctagaga tgcttttgga atgagacact      960
tgcgggctat tgatgtcaac atgaacaaaa tgcctgatgt agcaatgact cttgccgtcg     1020
ttgctctctt tgccgatggt ccaaccacca ttagagatgt ggctagctgg agagtaaagg     1080
agacggaaag gatgattgcc atttgcacag agcttagaaa actgggagct acagtggaag     1140
aaggttcaga ttattgtgtg attactccgc cgaaaaaggt gaaaccggca gagattgata     1200
cctatgatga tcatagaatg gcaatggcat tctctcttgc agcttgtgct gatgttccaa     1260
tcaccatcaa tgaccccggt tgcaccagga aaaccttccc cgactacttc caagtccttg     1320
aaagaatcac aaagcattaa                                                 1340

<210> SEQ ID NO 37
<211> LENGTH: 1347
<212> TYPE: DNA
<213> ORGANISM: Artificial sequence
<220> FEATURE:
<223> OTHER INFORMATION: variant TIPA EPSPS derived from lettuce

<400> SEQUENCE: 37
aagcccagca ccgctcccga ggaaatcgtg ctgcaaccga tcaaggagat cagcgggact       60
gtgaacctcc ctgggagtaa gtccctctct aataggatct tgcttctcgc ggcccttagt      120
gaagggacga ctgttgtgga caatctcttg aatagtgacg acgttcacta catgctcgga      180
gccctgcgcg ccctcggcct tcacgtcgaa gagaacggcg ccttgaagcg tgccatcgtc      240
gagggttgcg gcggtgtctt cccggttggc cgcgagtcca aggacgagat tcagctcttc      300
ttgggcaacg cggcatcgc gatgagggcg ctgacagccg cggttaccgc agccggaggc      360
agctcgtcct acatcctaga cggcgtgcct cggatgaggg aacgtcccat cggcgatctc      420
gtcaccgggc tcaagcaact tggcgctgac gtcgattgct tcctcgggac cgactgccca      480
ccggtcaggg tcgtcggctc cggtggactt cctggcggca aggtcaagct ctccggcagt      540
atctcctctc agtatctcac cgcgttactc atggcagctc cgcttgccct cggtgacgtc      600
gagatcgaga ttatcgacaa gctgatttcg ataccctacg tggaaatgac cctgaaactc      660
atggagcggt ttggcgtgtc cgtccagcac agcgatacgt gggataggtt ccacgtgcaa      720
ggcggtcaga agtacaagtc gccgggaaac gcctacgtcg agggcgacgc gtcgagcgcc      780
tcctacttcc tcgctggcgc tgccattacg ggcgggacca tcactgtgga gggttgcgga      840
acctcgtcac tccagggtga cgtgaagttt gctgaggttc tgggccagat gggtgcccaa      900
gtcacctgga cagagaactc cgttacggtg aagggtcctc ccagagatcc gtctgggagg      960
aagcaccttc gcccggtcga tgttaatatg aacaagatgc ccgacgtggc gatgacccta     1020
gcggttgtgg ccctgtacgc tgacggcccg actgccattc gtgacgtggc gtcgtggcgg     1080
```

```
gtcaaggaga cagaacggat gatcgctatc tgcaccgagc tacgaagct gggcgctacc    1140 gtcgaggagg gtccggacta ctgcatcatt acgccacccg agaaactaaa cgtcaccgct    1200
attgacacct acgacgatca tcgaatggct atggccttct cactggcagc gtgtgccgac    1260
gttgcggtta cgatcaaaga tccaggctgt acacgcaaga cgtttcccga ctatttcgag    1320
gtgctacagc ggttcgccaa gcactga                                        1347

<210> SEQ ID NO 38
<211> LENGTH: 1335
<212> TYPE: DNA
<213> ORGANISM: Artificial sequence
<220> FEATURE:
<223> OTHER INFORMATION: variant TIPT EPSPS coding sequence derived from
      Zea mays

<400> SEQUENCE: 38
gccggcgccg aggagatcgt gctgcagccc atcaaggaga tctccggcac cgtcaagctg    60
ccggggtcca gtcgcttttc caaccggatc ctcctactcg ccgccctgtc cgagggaca    120 acagtggttg ataacctgct gaacagtgag gatgtccact acatgctcgg ggccttgagg    180
actcttggtc tctctgtcga agcggacaaa gctgccaaaa gagctgtagt tgttggctgt    240
ggtggaaagt tcccagttga ggatgctaaa gaggaagtgc agctcttctt ggggaatgct    300
ggaattgcaa tgcggacatt gacagcagct gttactgctg ctggtggaaa tgcaacttac    360
gtgcttgatg gagtaccaag aatgagggag agacccattg cgacttggt tgtcggattg    420 aagcagcttg gtgcagatgt tgattgtttc cttggcactg actgcccacc tgttcgtgtc    480
aatggaatcg gagggctacc tggtggcaag gtcaagctgt ctggctccat cagcagtcag    540
tacttgagtg ccttgctgat ggctgctcct ttggctcttg gggatgtgga gattgaaatc    600
attgataaat taatctccat tccgtacgtc gaaatgacat tgagattgat ggagcgtttt    660
ggtgtgaaag cagagcattc tgatagctgg gacagattct acattaaggg aggtcaaaaa    720
tacaagtccc ctaaaaatgc ctatgttgaa ggtgatgcct caagcgcaag ctatttcttg    780
gctggtgctg caattactgg agggactgtg actgtgaaag ttgtggcac caccagtttg    840 cagggtgatg tgaagtttgc tgaggtactg gagatgatgg gagcgaaggt tacatggacc    900
gagactagcg taactgttac tggcccaccg cgggagccat tgggaggaa cacctcaag    960 gcgattgatg tcaacatgaa caagatgcct gatgtcgcca tgactcttgc tgtggttgcc    1020
ctctttgccg atgcccgac agccatcaga gacgtggctt cctggagagt aaaggagacc    1080
gagaggatgg ttgcgatccg gacggagcta accaagctgg gagcatctgt tgaggaaggg    1140
ccggactact gcatcatcac gccgccggag aagctgaacg tgacggcgat cgacacgtac    1200
gacgaccaca ggatggcgat ggccttctcc cttgccgcct gtgccgaggt ccccgtcacc    1260
atccggggcc ctgggtgcac ccggaagacc ttccccgact acttcgatgt gctgagcact    1320
ttcgtcaaga attaa                                                     1335

<210> SEQ ID NO 39
<211> LENGTH: 1308
<212> TYPE: DNA
<213> ORGANISM: Artificial sequence
<220> FEATURE:
<223> OTHER INFORMATION: variant TIPA EPSPS derived from Zea mays

<400> SEQUENCE: 39
atcaaggaga tctccggcac cgtcaagctg ccggggtcca gtcgcttttc caaccggatc    60
```

```
ctcctactcg ccgccctgtc cgaggggaca cagtggttg ataacctgct gaacagtgag    120
gatgtccact acatgctcgg ggccttgagg actcttggtc tctctgtcga agcggacaaa    180
gctgccaaaa gagctgtagt tgttggctgt ggtggaaagt tcccagttga ggatgctaaa    240
gaggaagtgc agctcttctt ggggaatgct ggaattgcaa tgcggcatt  gacagcagct    300
gttactgctg ctggtggaaa tgcaacttac gtgcttgatg gagtaccaag aatgagggag    360
agacccattg gcgacttggt tgtcggattg aagcagcttg gtgcagatgt tgattgtttc    420
cttggcactg actgcccacc tgttcgtgtc aatggaatcg gagggctacc tggtggcaag    480
gtcaagctgt ctggctccat cagcagtcag tacttgagtg ccttgctgat ggctgctcct    540
ttggctcttg gggatgtgga gattgaaatc attgataaat taatctccat tccgtacgtc    600
gaaatgacat tgagattgat ggagcgtttt ggtgtgaaag cagagcattc tgatagctgg    660
gacagattct acattaaggg aggtcaaaaa tacaagtccc ctaaaaatgc ctatgttgaa    720
ggtgatgcct caagcgcaag ctatttcttg gctggtgctg caattactgg agggactgtg    780
actgtggaag ttgtggcac  caccagtttg cagggtgatg tgaagtttgc tgaggtactg    840
gagatgatgg gagcgaaggt tacatggacc gagactagcg taactgttac tggcccaccg    900
cgggagccat ttgggaggaa acacctcaag gcgattgatg tcaacatgaa caagatgcct    960
gatgtcgcca tgactcttgc tgtggttgcc ctctttgccg atggcccgac agccatcaga    1020
gacgtggctt cctggagagt aaaggagacc gagaggatgg ttgcgatccg gacggagcta    1080
accaagctgg gagcatctgt tgaggaaggg ccggactact gcatcatcac gccgccggag    1140
aagctgaacg tgacggcgat cgacacgtac gacgaccaca ggatggcgat ggccttctcc    1200
cttgccgcct gtgccgaggt ccccgtcacc atccgggacc ctgggtgcac ccggaagacc    1260
ttccccgact acttcgatgt gctgagcact ttcgtcaaga attaatga               1308
```

<210> SEQ ID NO 40
<211> LENGTH: 51
<212> TYPE: DNA
<213> ORGANISM: Artificial sequence
<220> FEATURE:
<223> OTHER INFORMATION: mutagenesis primer

<400> SEQUENCE: 40
aatagcatgc ccggcgccga ggagatcgtg ctgcagccca tcaaggagat c            51

<210> SEQ ID NO 41
<211> LENGTH: 38
<212> TYPE: DNA
<213> ORGANISM: Artificial sequence
<220> FEATURE:
<223> OTHER INFORMATION: mutagenesis primer

<400> SEQUENCE: 41
attgaattcg agctcattaa ttcttgacga aagtgctc                           38

<210> SEQ ID NO 42
<211> LENGTH: 37
<212> TYPE: DNA
<213> ORGANISM: Artificial sequence
<220> FEATURE:
<223> OTHER INFORMATION: mutagenesis primer

<400> SEQUENCE: 42
gtttccacgg cgtgcatggc cggcgccgag gagatcg                            37

<210> SEQ ID NO 43

```
<211> LENGTH: 37
<212> TYPE: DNA
<213> ORGANISM: Artificial sequence
<220> FEATURE:
<223> OTHER INFORMATION: mutagenesis primer

<400> SEQUENCE: 43
cgatctcctc ggcgccggcc atgcacgccg tggaaac                              37

<210> SEQ ID NO 44
<211> LENGTH: 1341
<212> TYPE: DNA
<213> ORGANISM: Artificial sequence
<220> FEATURE:
<223> OTHER INFORMATION: variant TLPA EPSPS derived from Zea mays

<400> SEQUENCE: 44
tggcgggtgc cgaagaaatc gtgctgcagc cgatcaagga gatctccggc accgtcaagc     60
tgccggggtc caagtcgctt ccaaccgga tcctcctact cgccgccctg tccgagggga    120
caacagtggt tgataacctg ctgaacagtg aggatgtcca ctacatgctc ggggccttga    180
ggactcttgg tctctctgtc gaagcggaca agctgccaa agagctgta gttgttggct     240 gtggtggaaa gttcccagtt gaggatgcta agaggaagt gcagctcttc ttggggaatg     300
ctggacttgc aatgcgggca ttgacagcag ctgttactgc tgctggtgga aatgcaactt    360
acgtgcttga tggagtacca agaatgaggg agagacccat ggcgacttg gttgtcggat    420 tgaagcagct tggtgcagat gttgattgtt ccttggcac tgactgccca cctgttcgtg    480
tcaatggaat cggagggcta cctggtggca aggtcaagct gtctggctcc atcagcagtc    540
agtacttgag tgccttgctg atggctgctc ctttggctct tggggatgtg agattgaaa    600 tcattgataa attaatctcc attccgtacg tcgaaatgac attgagattg atggagcgtt    660
ttggtgtgaa agcagagcat tctgatagct gggacagatt ctacattaag ggaggtcaaa    720
aatacaagtc ccctaaaaat gcctatgttg aaggtgatgc ctcaagcgca agctatttct    780
tggctggtgc tgcaattact ggagggactg tgactgtgga aggttgtggc accaccagtt    840
tgcagggtga tgtgaagttt gctgaggtac tggagatgat gggagcgaag gttacatgga    900
ccgagactag cgtaactgtt actggcccac gcgggagcc atttggagg aaacacctca    960 aggcgattga tgtcaacatg aacaagatgc ctgatgtcgc catgactctt gctgtggttg   1020
ccctctttgc cgatggcccg acagccatca gagacgtggc ttcctggaga gtaaaggaga   1080
ccgagaggat ggttgcgatc cggacggagc taaccaagct gggagcatct gttgaggaag   1140
ggccggacta ctgcatcatc acgccgccgg agaagctgaa cgtgacggcg atcgacacgt   1200
acgacgacca caggatggcg atggccttct cccttgccgc ctgtgccgag gtccccgtca   1260
ccatccggga ccctgggtgc acccggaaga ccttccccga ctacttcgat gtgctgagca   1320
ctttcgtcaa gaattaatga c                                             1341

<210> SEQ ID NO 45
<211> LENGTH: 28
<212> TYPE: DNA
<213> ORGANISM: Artificial sequence
<220> FEATURE:
<223> OTHER INFORMATION: mutagenesis primer

<400> SEQUENCE: 45
gctggacttg caatgcgggc attgacag                                       28

<210> SEQ ID NO 46
```

```
<211> LENGTH: 28
<212> TYPE: DNA
<213> ORGANISM: Artificial sequence
<220> FEATURE:
<223> OTHER INFORMATION: mutagenesis primer

<400> SEQUENCE: 46
ctgtcaatgc cgcattgca agtccagc                                          28

<210> SEQ ID NO 47
<211> LENGTH: 1335
<212> TYPE: DNA
<213> ORGANISM: Zea Mays
<220> FEATURE:
<223> OTHER INFORMATION: Sense strand of Class I EPSPS gene

<400> SEQUENCE: 47
gcgggtgccg aagaaatcgt gctgcagccg atcaaggaga tctccggcac cgtcaagctg      60
ccggggtcca gtcgctttc caaccggatc ctcctactcg ccgccctgtc cgaggggaca      120
acagtggttg ataacctgct gaacagtgag gatgtccact acatgctcgg ggccttgagg     180
actcttggtc tctctgtcga agcggacaaa gctgccaaaa gagctgtagt tgttggctgt     240
ggtggaaagt tcccagttga ggatgctaaa gaggaagtgc agctcttctt ggggaatgct     300
ggaactgcaa tgcggccatt gacagcagct gttactgctg ctggtggaaa tgcaacttac     360
gtgcttgatg gagtaccaag aatgagggag agacccattg gcgacttggt tgtcggattg     420
aagcagcttg gtgcagatgt tgattgtttc cttggcactg actgcccacc tgttcgtgtc     480
aatggaatcg gagggctacc tggtggcaag gtcaagctgt ctggctccat cagcagtcag     540
tacttgagtg ccttgctgat ggctgctcct ttggctcttg gggatgtgga gattgaaatc     600
attgataaat taatctccat tccgtacgtc gaaatgacat tgagattgat ggagcgtttt     660
ggtgtgaaag cagagcattc tgatagctgg gacagattct acattaaggg aggtcaaaaa     720
tacaagtccc ctaaaaatgc ctatgttgaa ggtgatgcct caagcgcaag ctatttcttg     780
gctggtgctg caattactgg agggactgtg actgtggaag ttgtggcac caccagtttg     840 cagggtgatg tgaagtttgc tgaggtactg gagatgatgg gagcgaaggt tacatggacc     900
gagactagcg taactgttac tggcccaccg cgggagccat ttgggaggaa acacctcaag     960
gcgattgatg tcaacatgaa caagatgcct gatgtcgcca tgactcttgc tgtggttgcc    1020
ctctttgccg atggcccgac agccatcaga gacgtggctt cctggagagt aaaggagacc    1080
gagaggatgt tgcgatccg gacggagcta accaagctgg gagcatcgtg tgaggaaggg    1140
ccggactact gcatcatcac gccgccggag aagctgaacg tgacggcgat cgacacgtac    1200
gacgaccaca ggatggcgat ggccttctcc cttgccgcct gtgccgaggt ccccgtcacc    1260
atccgggacc ctgggtgcac ccggaagacc ttccccgact acttcgatgt gctgagcact    1320
ttcgtcaaga attaa                                                    1335

<210> SEQ ID NO 48
<211> LENGTH: 1335
<212> TYPE: DNA
<213> ORGANISM: Zea Mays
<220> FEATURE:
<223> OTHER INFORMATION: Antisense strand of Class I EPSPS gene

<400> SEQUENCE: 48
cgcccacggc ttctttagca cgacgtcggc tagttcctct agaggccgtg gcagttcgac      60
ggccccaggt tcagcgaaag gttggcctag gaggatgagc ggcgggacag gctcccctgt    120
```

-continued

```
tgtcaccaac tattggacga cttgtcactc ctacaggtga gtacgagcc ccggaactcc      180
tgagaaccag agagacagct tcgcctgttt cgacggtttt ctcgacatca acaaccgaca      240
ccacctttca agggtcaact cctacgattt ctccttcacg tcgagaagaa ccccttacga      300
ccttgacgtt acgccggtaa ctgtcgtcga caatgacgac gaccaccttt acgttgaatg      360
cacgaactac ctcatggttc ttactccctc tctgggtaac cgctgaacca acagcctaac      420
ttcgtcgaac cacgtctaca actaacaaag gaaccgtgac tgacgggtgg acaagcacag      480
ttaccttagc ctcccgatgg accaccgttc cagttcgaca gaccgaggta gtcgtcagtc      540
atgaactcac ggaacgacta ccgacgagga aaccgagaac ccctacacct ctaactttag      600
taactattta attagaggta aggcatgcag ctttactgta actctaacta cctcgcaaaa      660
ccacactttc gtctcgtaag actatcgacc ctgtctaaga tgtaattccc tccagttttt      720
atgttcaggg gattttacg gatacaactt ccactacgga gttcgcgttc gataaagaac      780
cgaccacgac gttaatgacc tccctgacac tgacaccttc caacaccgtg gtggtcaaac      840
gtcccactac acttcaaacg actccatgac ctctactacc ctcgcttcca atgtacctgg      900
ctctgatcgc attgacaatg accgggtggc gccctcggta aaccctcctt tgtggagttc      960
cgctaactac agttgtactt gttctacgga ctacagcggt actgagaacg acaccaacgg     1020
gagaaacggc taccgggctg tcggtagtct ctgcaccgaa ggacctctca tttcctctgg     1080
ctctcctacc aacgctaggc ctgcctcgat tggttcgacc ctcgtagaca actccttccc     1140
ggcctgatga cgtagtagtg cggcggcctc ttcgacttgc actgccgcta gctgtgcatg     1200
ctgctggtgt cctaccggta ccggaagagg gaacggcgga cacggctcca ggggcagtgg     1260
taggccctgg gacccacgtg ggccttctgg aaggggctga tgaagctaca cgactcgtga     1320
aagcagttct taatt                                                     1335
```

<210> SEQ ID NO 49
<211> LENGTH: 444
<212> TYPE: PRT
<213> ORGANISM: Zea Mays
<220> FEATURE:
<223> OTHER INFORMATION: Maize Class I EPSPS

<400> SEQUENCE: 49

```
Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
```

-continued

```
                145                 150                 155                 160
Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
                260                 265                 270

Glu Gly Cys Gly Thr Thr Ser Leu Gln Gly Asp Val Lys Phe Ala Glu
                275                 280                 285

Val Leu Glu Met Met Gly Ala Lys Val Thr Trp Thr Glu Thr Ser Val
        290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
                340                 345                 350

Ala Ser Trp Arg Val Lys Glu Thr Glu Arg Met Val Ala Ile Arg Thr
                355                 360                 365

Glu Leu Thr Lys Leu Gly Ala Ser Val Glu Glu Gly Pro Asp Tyr Cys
        370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
                420                 425                 430

Asp Tyr Phe Asp Val Leu Ser Thr Phe Val Lys Asn
        435                 440

<210> SEQ ID NO 50
<211> LENGTH: 448
<212> TYPE: PRT
<213> ORGANISM: Petunia
<220> FEATURE:
<223> OTHER INFORMATION: Class I EPSPS

<400> SEQUENCE: 50

Ala Thr Ala Gln Lys Pro Ser Glu Ile Val Leu Gln Pro Ile Lys Glu
1               5                   10                  15

Ile Ser Gly Thr Val Lys Leu Pro Gly Ser Lys Ser Leu Ser Asn Arg
                20                  25                  30

Ile Leu Leu Leu Ala Ala Leu Ser Glu Gly Thr Thr Val Val Asp Asn
        35                  40                  45

Leu Leu Ser Ser Asp Asp Ile His Tyr Met Leu Gly Ala Leu Lys Thr
    50                  55                  60

Leu Gly Leu His Val Glu Glu Asp Ser Ala Asn Gln Arg Ala Val Val
65              70                  75                  80
```

Glu Gly Cys Gly Gly Leu Phe Pro Val Gly Lys Glu Ser Lys Glu Glu
                    85                  90                  95

Ile Gln Leu Phe Leu Gly Asn Ala Gly Thr Ala Met Arg Pro Leu Thr
                100                 105                 110

Ala Ala Val Thr Val Ala Gly Gly Asn Ser Arg Tyr Val Leu Asp Gly
            115                 120                 125

Val Pro Arg Met Arg Glu Arg Pro Ile Ser Asp Leu Val Asp Gly Leu
130                 135                 140

Lys Gln Leu Gly Ala Glu Val Asp Cys Phe Leu Gly Thr Lys Cys Pro
145                 150                 155                 160

Pro Val Arg Ile Val Ser Lys Gly Gly Leu Pro Gly Gly Lys Val Lys
                165                 170                 175

Leu Ser Gly Ser Ile Ser Ser Gln Tyr Leu Thr Ala Leu Leu Met Ala
            180                 185                 190

Ala Pro Leu Ala Leu Gly Asp Val Glu Ile Glu Ile Asp Lys Leu
            195                 200                 205

Ile Ser Val Pro Tyr Val Glu Met Thr Leu Lys Leu Met Glu Arg Phe
    210                 215                 220

Gly Ile Ser Val Glu His Ser Ser Ser Trp Asp Arg Phe Phe Val Arg
225                 230                 235                 240

Gly Gly Gln Lys Tyr Lys Ser Pro Gly Lys Ala Phe Val Glu Gly Asp
                245                 250                 255

Ala Ser Ser Ala Ser Tyr Phe Leu Ala Gly Ala Ala Val Thr Gly Gly
            260                 265                 270

Thr Ile Thr Val Glu Gly Cys Gly Thr Asn Ser Leu Gln Gly Asp Val
        275                 280                 285

Lys Phe Ala Glu Val Leu Glu Lys Met Gly Ala Glu Val Thr Trp Thr
290                 295                 300

Glu Asn Ser Val Thr Val Lys Gly Pro Pro Arg Ser Ser Ser Gly Arg
305                 310                 315                 320

Lys His Leu Arg Ala Ile Asp Val Asn Met Asn Lys Met Pro Asp Val
                325                 330                 335

Ala Met Thr Leu Ala Val Val Ala Leu Tyr Ala Asp Gly Pro Thr Ala
            340                 345                 350

Ile Arg Asp Val Ala Ser Trp Arg Val Lys Glu Thr Glu Arg Met Ile
        355                 360                 365

Ala Ile Cys Thr Glu Leu Arg Lys Leu Gly Ala Thr Val Glu Glu Gly
    370                 375                 380

Pro Asp Tyr Cys Ile Ile Thr Pro Pro Glu Lys Leu Asn Val Thr Asp
385                 390                 395                 400

Ile Asp Thr Tyr Asp Asp His Arg Met Ala Met Ala Phe Ser Leu Ala
                405                 410                 415

Ala Cys Ala Asp Val Pro Val Thr Ile Asn Asp Pro Gly Cys Thr Arg
            420                 425                 430

Lys Thr Phe Pro Asn Tyr Phe Asp Val Leu Gln Gln Tyr Ser Lys His
        435                 440                 445

<210> SEQ ID NO 51
<211> LENGTH: 451
<212> TYPE: PRT
<213> ORGANISM: Glycine max
<220> FEATURE:
<223> OTHER INFORMATION: Soybean Class I EPSPS

<400> SEQUENCE: 51

```
Ala Ala Ala Glu Lys Pro Ser Thr Ala Pro Glu Ile Val Leu Glu Pro
  1               5                  10                  15
Ile Lys Asp Ile Ser Gly Thr Ile Thr Leu Pro Gly Ser Lys Ser Leu
             20                  25                  30
Ser Asn Arg Ile Leu Leu Leu Ala Ala Leu Ser Glu Gly Thr Thr Val
             35                  40                  45
Val Asp Asn Leu Leu Tyr Ser Glu Asp Ile His Tyr Met Leu Gly Ala
 50                  55                  60
Leu Arg Thr Leu Gly Leu Arg Val Glu Asp Asp Lys Thr Thr Lys Gln
 65                  70                  75                  80
Ala Ile Val Glu Gly Cys Gly Gly Leu Phe Pro Thr Ile Lys Glu Ser
                 85                  90                  95
Lys Asp Glu Ile Asn Leu Phe Leu Gly Asn Ala Gly Thr Ala Met Arg
                100                 105                 110
Pro Leu Thr Ala Ala Val Val Ala Ala Gly Gly Asn Ala Ser Tyr Val
            115                 120                 125
Leu Asp Gly Val Pro Arg Met Arg Glu Arg Pro Ile Gly Asp Leu Val
130                 135                 140
Ala Gly Leu Lys Gln Leu Gly Ala Asp Val Asp Cys Phe Leu Gly Thr
145                 150                 155                 160
Asn Cys Pro Pro Val Arg Val Asn Gly Lys Gly Gly Leu Pro Gly Gly
                165                 170                 175
Lys Val Lys Leu Ser Gly Ser Val Ser Ser Gln Tyr Leu Thr Ala Leu
                180                 185                 190
Leu Met Ala Ala Pro Leu Ala Leu Gly Asp Val Glu Ile Glu Ile Val
            195                 200                 205
Asp Lys Leu Ile Ser Val Pro Tyr Val Glu Met Thr Leu Lys Leu Met
210                 215                 220
Glu Arg Phe Gly Val Ser Val Glu His Ser Gly Asn Trp Asp Arg Phe
225                 230                 235                 240
Leu Val His Gly Gly Gln Lys Tyr Lys Ser Pro Gly Asn Ala Phe Val
                245                 250                 255
Glu Gly Asp Ala Ser Ser Ala Ser Tyr Leu Leu Ala Gly Ala Ala Ile
            260                 265                 270
Thr Gly Gly Thr Ile Thr Val Asn Gly Cys Gly Thr Ser Ser Leu Gln
            275                 280                 285
Gly Asp Val Lys Phe Ala Glu Val Leu Glu Lys Met Gly Ala Lys Val
290                 295                 300
Thr Trp Ser Glu Asn Ser Val Thr Val Ser Gly Pro Pro Arg Asp Phe
305                 310                 315                 320
Ser Gly Arg Lys Val Leu Arg Gly Ile Asp Val Asn Met Asn Lys Met
                325                 330                 335
Pro Asp Val Ala Met Thr Leu Ala Val Val Ala Leu Phe Ala Asn Gly
            340                 345                 350
Pro Thr Ala Ile Arg Asp Val Ala Ser Trp Arg Val Lys Glu Thr Glu
            355                 360                 365
Arg Met Ile Ala Ile Cys Thr Glu Leu Arg Lys Leu Gly Ala Thr Val
370                 375                 380
Glu Glu Gly Pro Asp Tyr Cys Val Ile Thr Pro Pro Glu Lys Leu Asn
385                 390                 395                 400
Val Thr Ala Ile Asp Thr Tyr Asp Asp His Arg Met Ala Met Ala Phe
                405                 410                 415
Ser Leu Ala Ala Cys Gly Asp Val Pro Val Thr Ile Lys Asp Pro Gly
                420                 425                 430
```

```
Cys Thr Arg Lys Thr Phe Pro Asp Tyr Phe Glu Val Leu Glu Arg Leu
            435                 440                 445

Thr Lys His
    450

<210> SEQ ID NO 52
<211> LENGTH: 427
<212> TYPE: PRT
<213> ORGANISM: Escherichia coli
<220> FEATURE:
<223> OTHER INFORMATION: Class I EPSPS

<400> SEQUENCE: 52

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335
```

-continued

```
Trp Arg Val Lys Glu Thr Asp Arg Leu Phe Ala Met Ala Thr Glu Leu
            340             345             350

Arg Lys Val Gly Ala Glu Val Glu Glu Gly His Asp Tyr Ile Arg Ile
            355             360             365

Thr Pro Pro Glu Lys Leu Asn Phe Ala Glu Ile Ala Thr Tyr Asn Asp
    370             375             380

His Arg Met Ala Met Cys Phe Ser Leu Val Ala Leu Ser Asp Thr Pro
385             390             395             400

Val Thr Ile Leu Asp Pro Lys Cys Thr Ala Lys Thr Phe Pro Asp Tyr
            405             410             415

Phe Glu Gln Leu Ala Arg Ile Ser Gln Ala Ala
            420             425
```

The invention claimed is:

1. A recombinant DNA molecule that encodes a glyphosate resistant class I EPSPS protein, wherein said glyphosate resistant class I EPSPS protein comprises a polypeptide sequence $GX_4X_1X_2RX_3$, where $X_1$ and $X_2$ are any amino acid, $X_4$ is isoleucine, and $X_3$ is selected from the group consisting of threonine, and alanine.

2. The DNA molecule of claim 1, wherein said DNA molecule is derived from a plant genome.

3. The DNA molecule of claim 2, wherein said DNA molecule is derived from Zea mays and is modified to encode for a glyphosate resistant class I EPSPS protein comprising an isoleucine at position 102 and an amino acid at position 106 selected from the group selected from threonine, and alanine.

4. The DNA molecule of claim 2, wherein said DNA molecule is derived from Arabidopsis and is modified to encode for said glyphosate resistant class I EPSPS protein comprising an isoleucine at position 102 and an alanine at position 106.

5. The DNA molecule of claim 2, wherein said DNA molecule is derived from Lettuce and is modified to encode for said glyphosate resistant class I EPSPS protein comprising an isoleucine at position 102 and an alanine at position 106.

6. The DNA molecule of claim 2, wherein said DNA molecule is derived from Zea mays and is modified to encode for said glyphosate resistant class I EPSPS protein comprising an isoleucine at position 102 and an alanine at position 106.

7. The DNA molecule of claim 2, wherein said DNA molecule is selected from the group consisting of SEQ ID NO:36, SEQ ID NO:37, SEQ ID NO:38, and SEQ ID NO: 39.

8. The DNA molecule of claim 1, wherein said DNA molecule is derived from a bacteria genome.

* * * * *

UNITED STATES PATENT AND TRADEMARK OFFICE
CERTIFICATE OF CORRECTION

| | | |
|---|---|---|
| PATENT NO. | : 8,436,159 B2 | Page 1 of 1 |
| APPLICATION NO. | : 12/688711 | |
| DATED | : May 7, 2013 | |
| INVENTOR(S) | : Alibhai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 327 days.

Signed and Sealed this
Twenty-third Day of December, 2014

Michelle K. Lee
*Deputy Director of the United States Patent and Trademark Office*